United States Patent
Hamilton et al.

(10) Patent No.: US 11,963,817 B2
(45) Date of Patent: Apr. 23, 2024

(54) WAVEFORM VISUALIZATION TOOL FOR FACILITATING MEDICAL DIAGNOSIS

(71) Applicant: Neurasignal, Inc., Los Angeles, CA (US)

(72) Inventors: Robert Hamilton, Los Angeles, CA (US); Corey Thibeault, Los Angeles, CA (US); Michael O'Brien, Los Angeles, CA (US); Mina Ranjbaran, Los Angeles, CA (US); Samuel Thorpe, Los Angeles, CA (US); Nicolas Canac, Los Angeles, CA (US)

(73) Assignee: Neurasignal, Inc., Los Angeles, CA (US)

( * ) Notice: Subject to any disclaimer, the term of this patent is extended or adjusted under 35 U.S.C. 154(b) by 0 days.

(21) Appl. No.: 15/971,260

(22) Filed: May 4, 2018

(65) Prior Publication Data
US 2019/0216433 A1    Jul. 18, 2019

Related U.S. Application Data

(60) Provisional application No. 62/619,015, filed on Jan. 18, 2018.

(51) Int. Cl.
*A61B 8/06* (2006.01)
*A61B 8/00* (2006.01)
(Continued)

(52) U.S. Cl.
CPC .............. *A61B 8/06* (2013.01); *A61B 8/0808* (2013.01); *A61B 8/0891* (2013.01);
(Continued)

(58) Field of Classification Search
None
See application file for complete search history.

(56) References Cited

U.S. PATENT DOCUMENTS 5,379,770 A * 1/1995 Van Veen ............... A61B 8/06
600/455
8,075,485 B2  12/2011 Smith
(Continued)

FOREIGN PATENT DOCUMENTS

JP    2006-025904 A    2/2006
WO    WO-92/07515 A1   5/1992
(Continued)

OTHER PUBLICATIONS

Moppet et al., "Transcranial Doppler Ultrasonography in Anaesthesia and Intensive Care", British Journal of Anaesthesia 93 (5): 710-24. 2004. (Year: 2004).*

(Continued)

*Primary Examiner* — Katherine L Fernandez
*Assistant Examiner* — Farouk A Bruce
(74) *Attorney, Agent, or Firm* — Polygon IP, LLP

(57) ABSTRACT

A tool for facilitating medical diagnosis is disclosed herein, including an ultrasound device configured to collect ultrasound data from a patient, a display device, and a processing circuit configured to generate a cerebral blood flow velocity (CBFV) waveform based on the ultrasound data, determine morphology indicators identifying attributes of the CBFV waveform, and configure the display device to display the CBFV waveform and the morphology indicators.

18 Claims, 13 Drawing Sheets

(51) Int. Cl.
*A61B 8/08* (2006.01)
*G01S 15/89* (2006.01)
(52) U.S. Cl.
CPC .......... *A61B 8/4218* (2013.01); *A61B 8/4227* (2013.01); *A61B 8/4236* (2013.01); *A61B 8/4245* (2013.01); *A61B 8/4281* (2013.01); *A61B 8/4477* (2013.01); *A61B 8/461* (2013.01); *A61B 8/463* (2013.01); *A61B 8/488* (2013.01); *A61B 8/5207* (2013.01); *A61B 8/5292* (2013.01); *A61B 8/0816* (2013.01); *A61B 8/466* (2013.01); *A61B 8/5223* (2013.01); *G01S 15/8979* (2013.01)

(56) References Cited

U.S. PATENT DOCUMENTS

| | | | |
|---|---|---|---|
| 2002/0177843 | A1 | 11/2002 | Anderson et al. |
| 2003/0032869 | A1 | 2/2003 | Muramatsu et al. |
| 2004/0243006 | A1* | 12/2004 | Nakata ............... A61B 8/06 600/485 |
| 2004/0267120 | A1 | 12/2004 | Podany et al. |
| 2005/0015009 | A1* | 1/2005 | Mourad ............... A61B 5/031 600/438 |
| 2005/0240102 | A1 | 10/2005 | Rachlin et al. |
| 2005/0261582 | A1 | 11/2005 | Becker et al. |
| 2006/0052704 | A1 | 3/2006 | Baba et al. |
| 2006/0184034 | A1 | 8/2006 | Haim et al. |
| 2008/0021318 | A1 | 1/2008 | Kato et al. |
| 2008/0214939 | A1 | 9/2008 | Harhen |
| 2008/0221452 | A1 | 9/2008 | Njemanze |
| 2009/0076404 | A1 | 3/2009 | Hopenfeld |
| 2009/0131805 | A1* | 5/2009 | O'Brien ............ A61B 5/02028 600/485 |
| 2010/0125213 | A1* | 5/2010 | Lo ............... A61B 5/02028 600/500 |
| 2010/0249598 | A1 | 9/2010 | Smith et al. |
| 2011/0201961 | A1 | 8/2011 | Hu et al. |
| 2012/0136255 | A1 | 5/2012 | Fan et al. |
| 2012/0165675 | A1 | 6/2012 | Syme |
| 2012/0265196 | A1 | 10/2012 | Turner et al. |
| 2013/0095701 | A1 | 4/2013 | Golko et al. |
| 2013/0245451 | A1 | 9/2013 | Mochizuki et al. |
| 2014/0180128 | A1 | 6/2014 | Corl |
| 2014/0343431 | A1* | 11/2014 | Vajinepalli ............... A61B 8/06 600/454 |
| 2015/0025390 | A1 | 1/2015 | Hewitt et al. |
| 2015/0208159 | A1 | 7/2015 | Sander et al. |
| 2016/0256130 | A1 | 9/2016 | Hamilton et al. |
| 2016/0278736 | A1 | 9/2016 | Hamilton et al. |
| 2017/0086789 | A1 | 3/2017 | Brandl et al. |
| 2017/0086792 | A1* | 3/2017 | Chono ................ A61B 8/463 |
| 2017/0188993 | A1 | 7/2017 | Hamilton et al. |
| 2017/0215811 | A1 | 8/2017 | Newberry |
| 2018/0103862 | A1 | 4/2018 | Kim |
| 2018/0240543 | A1 | 8/2018 | Maeda et al. |
| 2019/0216433 | A1 | 7/2019 | Hamilton et al. |

FOREIGN PATENT DOCUMENTS

| | | | |
|---|---|---|---|
| WO | WO-9724986 A2 * | 7/1997 | ............... A61B 8/06 |
| WO | WO-2008/091938 A1 | 7/2008 | |
| WO | WO-2015/073903 A1 | 5/2015 | |
| WO | WO-2016/171476 A1 | 10/2016 | |

OTHER PUBLICATIONS

Jang et al., "A Real-Time Pulse Peak Detection Algorithm for the Photoplethysmogram", International Journal of Electronics and Electrical Engineering, vol. 2, No. Mar. 1, 2014, pp. 45-49.

Non-Final Office Action dated Sep. 19, 2018, from U.S. Appl. No. 15/987,804.
Non-Final Office Action dated Sep. 28, 2018, from U.S. Appl. No. 16/003,012.
Final Office Action dated Jan. 2, 2019, from U.S. Appl. No. 15/987,804.
Final Office Action dated Jan. 2, 2019, from U.S. Appl. No. 16/003,012.
Chia-Chi Chang et al: "Quantitative Non-Stationary Assessment of Cerebral Hemodynamics by Empirical Mode Decomposition of Cerebral Doppler Flow Veolocity", Advances in Adaptive Data Analysis, vol. 05, No. 01, Jan. 1, 2013 (Jan. 1, 2013), p. 1350002, XP055510620, ISSN: 1793-5369, DOI: 10.1142/S1793536913500027.
International Search Report and Written Opinion dated Oct. 9, 2018, from application No. PCT/US2018/031069.
Vaitkus P J et al: "Development of Methods to Analyse Transcranial Doppler Ultrasound Signals Recorded in Microgravity", Medical and Biological Engineering and Computing, Springer, Heildelberg, DE, vol. 28, No. 4, Jul. 1, 1990 (Jul. 1, 1990), pp. 306-311, XP000136091, ISSN: 0140-0018, DOI: 10.1007/BF02446147.
Final Office Action dated Aug. 6, 2019, from U.S. Appl. No. 16/003,012.
Non-Final Office Action dated Mar. 21, 2019, from U.S. Appl. No. 15/987,804.
Non-Final Office Action dated Mar. 7, 2019, from U.S. Appl. No. 16/003,012.
Final Office Action dated Feb. 28, 2020, from U.S. Appl. No. 16/255,531.
Final Office Action dated Jan. 13, 2020, from U.S. Appl. No. 16/254,416.
International Search Report and Written Opinion dated Apr. 12, 2019, from application No. PCT/US2019/014802.
International Search Report and Written Opinion dated Mar. 27, 2019, from application No. PCT/US2019/014587.
Ni, et al., "Serial Transcranial Doppler Sonography in Ischemic Strokes in Middle Cerebral Artery Territory" Journal of Neuroimaging, Oct. 1, 1994, pp. 232-236.
Non-Final Office Action dated Aug. 22, 2019, from U.S. Appl. No. 16/255,531.
Non-Final Office Action dated Jul. 12, 2019, from U.S. Appl. No. 16/254,416.
Saqqur, et al., "Derivation of Power M-Mode Transcranial Doppler Criteria for Angiographic Proven MCA Occlusion", Journal of Neuroimaging, vol. 16, No. 4, Oct. 1, 2006, pp. 323-328.
Thorpe, et al., "Decision Criteria for Large Vessel Occlusion Using Transcranial Doppler Waveform Morphology", Frontiers in Neurology, vol. 9, Oct. 17, 2018.
Interntional Preliminary Report on Patentability dated Jul. 30, 2020, from application No. PCT/US2018/031069.
Notice of Allowance dated Jul. 24, 2020, from U.S. Appl. No. 16/003,012.
Notice of Allowance dated May 24, 2021, from U.S. Appl. No. 16/254,416.
Final Office Action dated Feb. 3, 2021, from U.S. Appl. No. 16/254,416.
U.S. Non-Final Office Action dated Sep. 29, 2022, from U.S. Appl. No. 17/486,300.
U.S. Non-Final Office Action dated Oct. 6, 2022, from U.S. Appl. No. 17/107,843.
Australian Re-examination Report dated Dec. 21, 2022, for application No. 2019210133.
Purvis et al., Transcranial Doppler Investigation of Hemodynamic Alterations Associated with Blunt Cervical Vascular Injuries in Trauma Patients:, Journal of Ultrasound Medicine, vol. 32, pp. 1759-1768, 2013 (Year 2013).
U.S. Final Office Action dated Mar. 20, 2023, for U.S. Appl. No. 17/107,843.
U.S. Notice of Allowance dated Mar. 8, 2023, for U.S. Appl. No. 17/486,300.

* cited by examiner

WAVEFORM VISUALIZATION TOOL FOR FACILITATING MEDICAL DIAGNOSIS

CROSS-REFERENCE TO RELATED PATENT APPLICATION

The present disclosure claims priority to, and the benefit of, U.S. provisional patent application Ser. No. 62/619,015, titled WAVEFORM VISUALIZATION TOOL FOR FACILITATING MEDICAL DIAGNOSIS, and filed on Jan. 18, 2018, which is incorporated herein by reference in its entirety.

FIELD

Subject matter described herein relates generally to medical devices, and more particularly to a headset including a transducer and an output device for diagnosing medical conditions.

BACKGROUND

Clinical guidelines recommend monitoring for medical conditions including stroke, emboli, stenosis, vasospasm as well as elevated intracranial pressure (ICP) which may alter cerebral blood flow. For instance, monitoring is performed for patients with severe traumatic brain injury (TBI), subarachnoid hemorrhage (SAH), and other conditions with a considerable risk of elevated ICP, because elevated ICP can lead to death or serious injury. Conventionally, a reliable method for monitoring a patient's ICP is a neurosurgeon invasively placing a pressure probe into the brain tissue or cerebral ventricles. Such method is costly, invasive, prone to infection, and is limited to in-hospital usage. As a result, ICP monitoring is infrequently performed.

Transcranial Doppler (TCD) devices can perform non-invasive, cerebral blood flow monitoring using ultrasound which can be used for a number of medical conditions including those listed above. However, displays and screens on conventional TCDs show simple waveforms without any diagnostic visualization that can assist a physician with equipment calibration or diagnosis in real-time.

Acquiring the cerebral blood flow velocity (CBFV) signals using TCD requires placement of a transducer within a specific region of the skull thin enough for the ultrasound waves to penetrate, locating a signal of the artery of interest, and maintaining a steady position for sufficient sample size. The location of these narrow windows varies significantly from person to person. Additionally, reading and interpreting the scans once complete is difficult because subtle features and changes in the CBFV waveforms that indicate neurological disorders are not easily discernible using traditional TCD analysis or visual inspection. These requirements make insonating (i.e., exposing to ultrasound) the desired blood vessel difficult, thus restricting TCD use to major hospitals with expensive, on staff expert human sonographers to operate the device as well as reducing the overall utility of the device through utilization of only simple analysis.

With respect to stroke detection, interventional (e.g., stentriever) and pharmaceutical (e.g., tissue plasminogen activator (tPA)) treatments for large vessel occlusion (LVO) need to be administered within a short duration from symptom onset. Conventional standards for stroke diagnosis involves computed tomography angiography (CTA) machines, which are limited to in-hospital uses and a small number of stroke ambulances, due to high cost, requirement of expert operators, and intravenous (IV) injection of iodine-rich contrast material.

SUMMARY

In some arrangements, a tool for facilitating medical diagnosis includes an ultrasound device, wherein the ultrasound device is configured to collect ultrasound data from a patient, a display device, and a processing circuit configured to generate a CBFV waveform based on the ultrasound data, determine morphology indicators identifying attributes of the CBFV waveform, and configure the display device to display the CBFV waveform and the morphology indicators.

In some arrangements, the display device is configured to display the CBFV waveform and the morphology indicators in real time or semi-real time as the ultrasound data is being collected.

In some arrangements, the processing circuit generates the CBFV waveform based on the ultrasound data by generating a plurality of CBFV waveforms based on the ultrasound data, each CBFV waveform corresponding to a pulse, and the CBFV waveform used for morphology calculation is derived from the plurality of CBFV waveforms.

In some arrangements, configuring the display device to display the CBFV waveform and the morphology indicators includes configuring the display device to display the plurality of CBFV waveforms in a first display window.

In some arrangements, configuring the display device to display the CBFV waveform and the morphology indicators includes configuring the display device to display the CBFV waveform and the morphology indicators in a second display window.

In some arrangements, the tool further includes deriving the CBFV waveform from the plurality of CBFV waveforms by one or more of filtering the plurality of CBFV waveforms and averaging the plurality of CBFV waveforms.

In some arrangements, determining the morphology indicators identifying the attributes of the CBFV waveform includes segmenting a plurality detected CBFV waveforms into distinct CBFV waveforms, and identifying the attributes for the CBFV waveform that is an average of the distinct CBFV waveforms.

In some arrangements, the attributes include at least one peak on the CBFV waveform.

In some arrangements, configuring the display device to display the CBFV waveform and the morphology indicators includes configuring the display device to display a peak indicator corresponding to each of the at least one peak of the CBFV waveform.

In some arrangements, the processing circuit is further configured to use machine learning to determine that the patient is experiencing a medical condition based on the morphology indicators, and configure the display device to display a notification related to the medical condition.

In some arrangements, in response to determining that the patient is experiencing the medical condition, the processing circuit is further configured to send an email, a page, or a short message service (SMS) message to an operator, or call the operator.

In some arrangements, in response to determining that the patient is experiencing the medical condition, the processing circuit further configures a medical device to administer a drug to treat the medical condition.

In some arrangements, the processing circuit is further configured to determine that a probe of the ultrasound device is misaligned based on the morphology indicators, and automatically adjust a position of the probe.

In some arrangements, the processing circuit determines that the probe of the ultrasound device is misaligned based on machine learning.

In some arrangements, a method for facilitating medical diagnosis, includes collecting, with an ultrasound device, ultrasound data from a patient, generating a CBFV waveform based on the ultrasound data, determining morphology indicators identifying attributes of the CBFV waveform, and displaying the CBFV waveform and the morphology indicators.

In some arrangements, the CBFV waveform and the morphology indicators are displayed in real time or semi-real time as the ultrasound data is being collected.

In some arrangements, the CBFV waveform is generated by generating a plurality of CBFV waveforms based on the ultrasound data, each CBFV waveform corresponding to a pulse, and deriving the CBFV waveform from the plurality of CBFV waveforms.

In some arrangements, displaying the CBFV waveform and the morphology indicators includes displaying the plurality of CBFV waveforms in a first display window, and displaying the CBFV waveform and the morphology indicators in a second display window.

In some arrangements, determining the morphology indicators identifying the attributes of the CBFV waveform includes segmenting a plurality detected CBFV waveforms into distinct CBFV waveforms, and identifying the attributes for the CBFV waveform that is an average of the distinct CBFV waveforms.

In some arrangements, the attributes include at least one peak on the CBFV waveform, and displaying the CBFV waveform and the morphology indicators includes displaying a peak indicator corresponding to each of the at least one peak of the CBFV waveform.

In some arrangements, a non-transitory processor-readable medium storing processor-readable instructions such that, when executed, causes a processor to facilitate medical diagnosis by collecting ultrasound data from a patient, generating a CBFV waveform based on the ultrasound data, determining morphology indicators identifying attributes of the CBFV waveform, and displaying the CBFV waveform and the morphology indicators.

BRIEF DESCRIPTION OF THE FIGURES

Features, aspects, and advantages of the present invention will become apparent from the following description and the accompanying example arrangements shown in the drawings, which are briefly described below.

DETAILED DESCRIPTION

Figure 1:
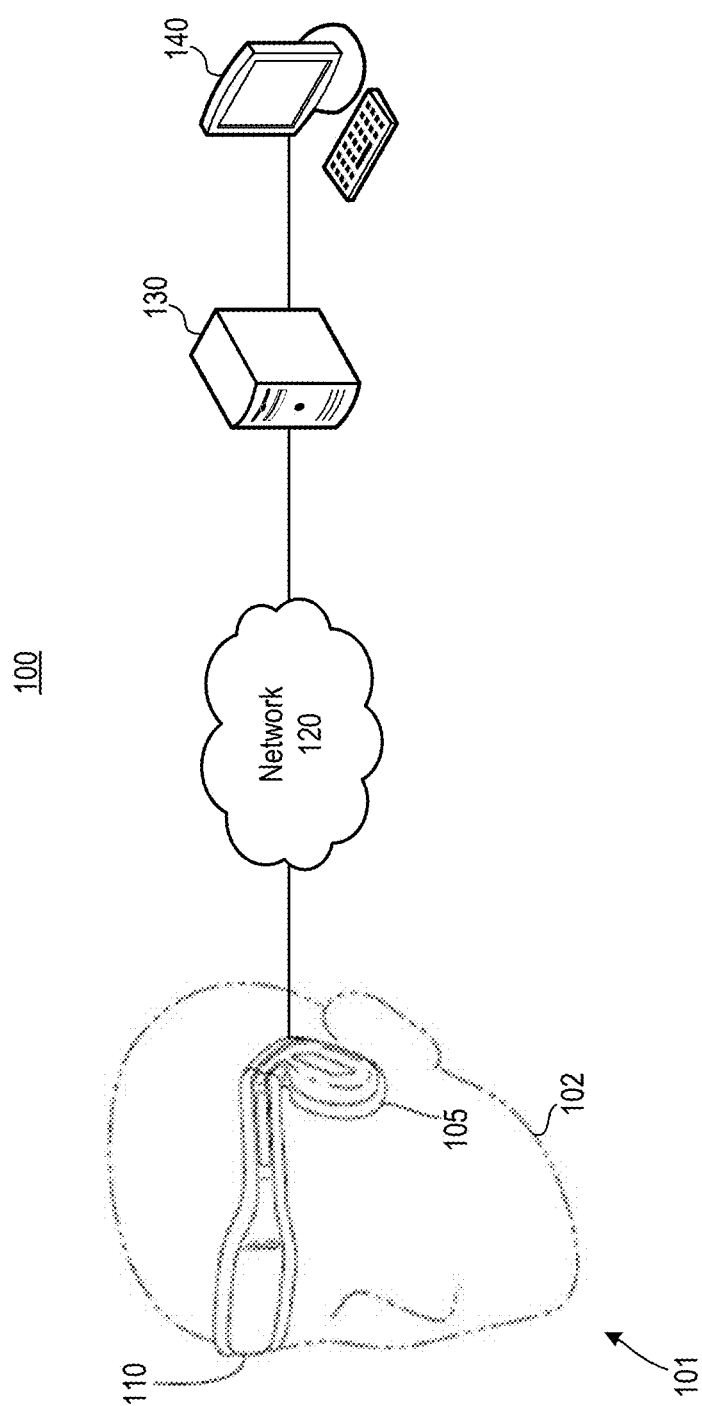
FIG. 1 is a schematic diagram illustrating a waveform visualization system according to various arrangements.

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various arrangements, reference is made to the accompanying drawings which form a part hereof and in which are shown, by way of illustration, specific arrangements in which the arrangements may be practiced. It is to be understood that other arrangements may be utilized, and structural changes may be made without departing from the scope of the various arrangements disclosed in the present disclosure.

Arrangements described herein relate to apparatuses, systems, methods, and non-transitory computer-readable medium that provide affordable, non-invasive TCD devices in hospital and field-based (pre-hospital) settings. Such TCD devices can be used for continuously monitoring CBFV, among other parameters. As a diagnostic tool that assists a physician with equipment calibration (e.g., probe positioning) or diagnosis in real-time or semi-real time, arrangements described herein include a TCD ultrasound device configured to measure CBFV. The TCD ultrasound device is operatively coupled to a display screen configured to display visual indicators that identify the morphology of the CBFV waveforms in the CBFV output in real-time or semi-real time, to assist an operator with equipment calibration (e.g., probe positioning) and diagnosis. Such arrangements are directed to improving TCD devices by presenting useful morphological information to the operator. The operator conventionally uses his or her human judgment to determine whether a CBFV waveform as a whole appears to be problematic, without being able to identify morphological attributes for detailed analysis in real-time or semi-real-time.

In addition, the equipment calibration and diagnosis based on CBFV waveform indicators can be automatically executed, in addition or alternative to displaying the visual indicators to the operator. No conventional medical devices can perform automated equipment calibration or diagnosis based on the CBFV waveform indicators. Thus, such arrangements automate a process not previously automated.

Arrangements described herein relate to apparatuses, systems, methods, and non-transitory computer-readable medium that provide a standardized, quantitative, and non-invasive diagnostic tool capable of providing improved large vessel occlusion (LVO) identification in hospital and field-based (pre-hospital) settings. Such a diagnostic tool includes TCD devices coupled with machine learning for rapid stroke diagnosis and allows a patient to be monitored while en route to a hospital, thus bridging a gap between incidence detection and hospital treatment.

FIG. 1 is a schematic diagram illustrating a waveform visualization system 100 according to various arrangements. Referring to FIG. 1, the waveform visualization system 100 includes at least a headset device 110, a controller 130, and an output device 140.

The headset device 110 is a TCD ultrasound device configured to emit and measure acoustic energy in a head 102 of a patient 101. An example of the headset device 110 is a supine headset device. The headset device 110 includes at least one probe 105 (e.g., at least one ultrasound probe) configured to emit and measure ultrasound acoustic energy in the head 102. For example, the probe 105 includes at least one TCD scanner, which can automatically locate the middle cerebral artery (MCA) in some arrangements. At least one probe 105 can be positioned in a temporal window region (temple) of the head 102 to collect the ultrasound data. In other arrangements, the probe can be positioned over different acoustic windows such as the transorbital window or the suboccipital window. In some arrangements, headset 110 includes two ultrasound probes 105, which can be placed on the temporal window region on both sides of the head 102. A headband, strap, Velcro®, hat, helmet, or another suitable wearable structure of the like connects the two probes in such arrangements. A lubricating gel can be applied between the head 102 and the probe 105 to improve acoustic transmission.

The controller 130 is configured to receive the ultrasound data outputted by the headset device 110 and to generate CBFV waveforms that correspond to the ultrasound data. In that regard, the probe 110 is operatively coupled to the controller 130 via a suitable network 120 to send the ultrasound data to the controller 130. The network 120 can be wired or wireless (e.g., 802.11X, ZigBee, Bluetooth®, Wi-Fi, or the like). The controller 130 can further perform signal processing functions to determine and display morphological indicators corresponding to the CBFV waveforms to facilitate a physician, clinician, technician, or care provider with diagnosis and/or to adjust the positioning of the headset device 110 and the probe 105. Further, as described, the headset device 110 can automatically adjust the position and orientation of the probe 105 responsive to determination that the probe 105 is not optimally placed based on the morphological indicators in the manner described herein. In some arrangements, the controller 130, the output device 140, and a portion of the network 120 are incorporated into a single device (e.g., a touchscreen tablet device).

In some arrangements, the output device 140 includes any suitable device configured to display information, results, messages, and the like to an operator (e.g., a physician, clinician, technician, or care provider) of the waveform visualization system 100. For example, the output device 140 includes but is not limited to, a monitor, a touchscreen, or any other output device configured to display the CBFV waveforms, the morphology indicators, and the like for facilitating diagnosis and/or the positioning of the headset device 110 and the probe 105 relative to the head 102 in the manner described.

Figure 2:
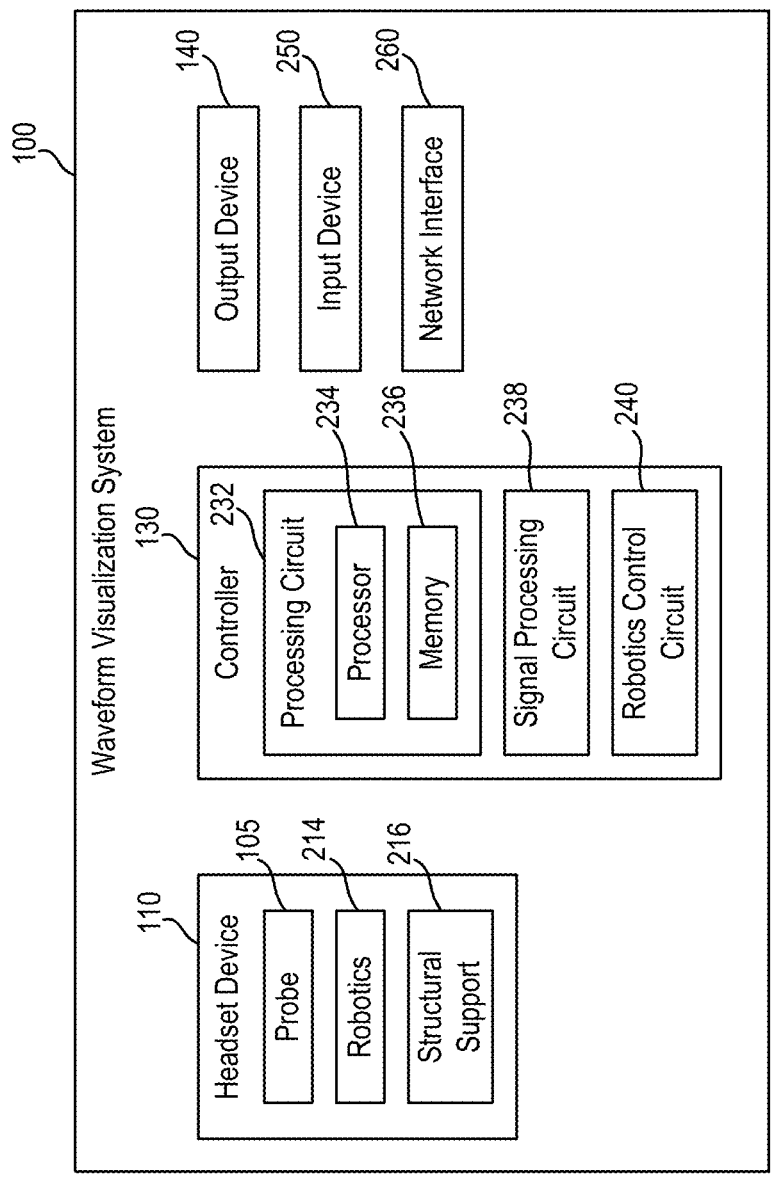
FIG. 2 is a schematic block diagram illustrating a waveform visualization system according to various arrangements.

FIG. 2 is a schematic block diagram illustrating the waveform visualization system 100 (FIG. 1) according to various arrangements. Referring to FIGS. 1-2, the headset device 110 includes the probe 105 as described. Further disclosure regarding examples of the probe 105 that can be used in conjunction with the waveform visualization system 100 described herein can be found in non-provisional patent application Ser. No. 15/399,648, titled ROBOTIC SYSTEMS FOR CONTROL OF AN ULTRASONIC PROBE, and filed on Jan. 5, 2017, which is incorporated herein by reference in its entirety. In some arrangements, the headset device 110 includes manually operated probes, as opposed to automatically or robotically-operated probes.

In some arrangements, the headset device 110 includes robotics 214 configured to control positioning of the probe 105. For example, the robotics 214 are configured to translate the probe 105 along a surface of the head 102 and to move the probe 105 with respect to (e.g., toward and away from) the head 102 along various axes in the Cartesian, spherical, and rotational coordinate systems. In particular, the robotics 214 can include a multiple degree of freedom (DOF) TCD transducer positioning system with motion planning. In some embodiments, the robotics 214 are capable of supporting two, three, four, five, or six DOF movements of the probe 105 with respect to the head 102. In some instances, the robotics 214 can translate in X and Y axes (e.g., along a surface of the head 102) to locate a temporal window region in translational axes, and in Z axis with both force and position feedback control to both position, and maintain the appropriate force against the skull/skin to maximize signal quality by maintaining appropriate contact force. Two angular DOF (e.g., pan and tilt) may be used to maximize normal insonation of blood vessels to maximize velocity signals.

In some arrangements, an end of the probe 105 is operatively coupled to or otherwise interfaces with the robotics 214. The robotics 214 include components, such as but not limited to a motor assembly and the like for controlling the positioning of the probe 105 (e.g., controlling z-axis pressure, normal alignment, or the like of the probe 105). In some arrangements, the registration of the probe 105 against the head 105 is accomplished using the robotics 214 to properly position and align the probe 105 in the manner described.

In some arrangements, the probe 105 includes a first end and a second end that is opposite to the first end. In some arrangements, the first end includes a concave surface that is configured to be adjacent to or contact a scanning surface on the head 102. The concave surface is configured with a particular pitch to focus generated energy towards the scanning surface. In some arrangements, the headset device 110 is a TCD apparatus such that the first end of the probe 105 is configured to be adjacent to or contact and align along a side of the head 102. The first end of the probe 105 is configured to provide ultrasound wave emissions from the first end and directed into the head 102 (e.g., toward the brain). For example, the first end of the probe 105 can include a transducer (such as, but not limited to, an ultrasound transducer, TCD, transcranial color-coded sonography (TCCS), or acoustic ultrasound transducer array such as sequential arrays or phased arrays) that emits acoustic energy capable of penetrating windows in the skull/head or neck. In other arrangements, the probe 105 is configured to emit other types of waves during operation, such as, but not limited to, infrared (IR), near-infrared spectroscopy (NIRS), electro-magnetic, x-rays, or the like.

In some arrangements, the second end of the probe 105 is coupled to the robotics 214. In some arrangements, the second end of the probe 105 includes a threaded section along a portion of the body of the probe 105. The second end is configured to be secured in the robotics 214 via the threads (e.g., by being screwed into the robotics 214). In other arrangements, the probe 105 is secured in the robotics 214 by any other suitable connecting means, such as but not limited to welding, adhesive, one or more hooks and latches, one or more separate screws, press fittings, or the like.

The headset device 110 can further include a structural support 216 configured to support the head 102 of the patient 101 and/or to support the headset device 110 on the head 102 or other parts of a body of the patient 101. In some examples, the structural support 216 includes a platform (e.g., a baseplate) that allows the patient 101 to lay down on a flat surface in a reclined or supine position while the headset device 110 is operational. Further disclosure regarding such implementation of the structural support 216 that can be used in conjunction with the waveform visualization system 100 described herein can be found in non-provisional patent application Ser. No. 15/853,433, titled HEADSET SYSTEM, and filed on Dec. 22, 2017, which is incorporated herein by reference in its entirety. In other examples, the structural support 216 includes one or more of a mount, cradle, headband, strap, Velcro®, hat, helmet, or another suitable wearable structure of the like such that the patient 101 can wear the headset device 110 on the head 102, shoulders, neck, and/or the like when the patient 101 is sitting, standing, or lying down. The structural support 216 can be made from any suitably malleable material that allows for flexing, such as, but not limited to, flexible plastics, polyethylene, urethanes, polypropylene, ABS, nylon, fiber-reinforced silicones, structural foams, or the like.

While the headset device 110 is shown and described as a headset such that the headset device 110 is lightweight and portable, one of ordinary skill in the art recognizes that the headset device 110 can be implemented with other types of TCD devices.

In some arrangements, the waveform visualization system 100 includes an input device 250. The input device 250 includes any suitable device configured to allow an operator, physician, or care provider personnel to input information or commands into the waveform visualization system 100. In some arrangements, the input device 250 includes but is not limited to, a keyboard, a keypad, a mouse, a joystick, a touchscreen display, or any other input device performing a similar function. In some arrangements, the input device 250 and the output device 140 can be a same input/output device (e.g., a touchscreen display device).

In some arrangements, the network interface 260 is structured for sending and receiving data (e.g., results, instructions, requests, software or firmware updates, and the like) over a communication network. Accordingly, the network interface 260 includes any of a cellular transceiver (for cellular standards), local wireless network transceiver (for 802.11X, ZigBee, Bluetooth®, Wi-Fi, or the like), wired network interface, a combination thereof (e.g., both a cellular transceiver and a Bluetooth transceiver), and/or the like. In some examples, the network interface 260 includes any method or device configured to send data from the headset device 110 to the controller 130. In that regard, the network interface 260 may include Universal Serial Bus (USB), FireWire, serial communication, and the like.

In some arrangements, the input device 250, the output device 140, the network interface 260, and the controller 130 form a single computing system that resides on a same node on the network 120, and the headset device 110 is connected to the computing system via the network 120, the network interface 260 is configured to communicate data to and from the headset device 110 via the network 120. In such arrangements, the headset device 110 includes a similar network interface (not shown) to communicate data to and from the computing device via the network 120. In other arrangements in which the headset device 110, the controller 130, the output device 140, the input device 250, and the network interface 260 all reside in a same computing device on a same node of a network, the network interface 260 is configured to communicate data with another suitable computing system (e.g., cloud data storage, remote server, and the like).

In some arrangements, the controller 130 is configured for controlling operations, processing data, executing input commands, providing results, and the like with respect to the waveform visualization system 100, and in particular, in relation to the morphology indicators as described herein. For example, the controller 130 is configured to receive input data or instructions from the input device 250 or the network interface 260, to control the waveform visualization system 100 to execute the commands, to receive data from the headset device 110, to provide information (e.g., the CBFV waveforms and the morphology indicators) to the output device 140 or network interface 260, and so on.

The controller 130 includes a processing circuit 232 having a processor 234 and a memory 236. In some arrangements, the processor 234 can be implemented as a general-purpose processor and is coupled to the memory 236. The processor 234 includes any suitable data processing device, such as a microprocessor. In the alternative, the processor 234 includes any suitable electronic processor, controller, microcontroller, or state machine. In some arrangements, the processor 234 is implemented as a combination of computing devices (e.g., a combination of a Digital Signal Processor (DSP) and a microprocessor, a plurality of microprocessors, at least one microprocessor in conjunction with a DSP core, or any other such configuration). In some arrangements, the processor 234 is implemented as an Application Specific Integrated Circuit (ASIC), one or more Field Programmable Gate Arrays (FPGAs), a Digital Signal Processor (DSP), a group of processing components, or other suitable electronic processing components.

In some arrangements, the memory 236 includes a non-transitory processor-readable storage medium that stores processor-executable instructions. In some arrangements, the memory 236 includes any suitable internal or external device for storing software and data. Examples of the memory 236 include but are not limited to, Random Access Memory (RAM), Read-Only Memory (ROM), Non-Volatile RAM (NVRAM), flash memory, floppy disks, hard disks, dongles or other Recomp Sensor Board (RSB)-connected memory devices, or the like. The memory 236 can store an Operating System (OS), user application software, and/or executable instructions. The memory 236 can also store application data, such as an array data structure. In some arrangements, the memory 236 stores data and/or computer code for facilitating the various processes described herein.

As used herein, the term "circuit" can include hardware structured to execute the functions described herein. In some arrangements, each respective circuit can include machine-readable media for configuring the hardware to execute the functions described herein. The circuit can be embodied as one or more circuitry components including, but not limited to, processing circuitry, network interfaces, peripheral devices, input devices, output devices, sensors, etc. In some arrangements, a circuit can take the form of one or more analog circuits, electronic circuits (e.g., integrated circuits (IC), discrete circuits, system on a chip (SOCs) circuits, etc.), telecommunication circuits, hybrid circuits, and any other suitable type of circuit. In this regard, the circuit can include any type of component for accomplishing or facilitating achievement of the operations described herein. For example, a circuit as described herein can include one or more transistors, logic gates (e.g., NAND, AND, NOR, OR, XOR, NOT, XNOR, etc.), resistors, multiplexers, registers, capacitors, inductors, diodes, wiring, and so on.

The circuit can also include one or more processors communicatively coupled to one or more memory or memory devices. In this regard, the one or more processors can execute instructions stored in the memory or can execute instructions otherwise accessible to the one or more processors. In some arrangements, the one or more processors can be embodied in various ways. The one or more processors can be constructed in a manner sufficient to perform at least the operations described herein. In some arrangements, the one or more processors can be shared by multiple circuits (e.g., a first circuit and a second circuit can comprise or otherwise share the same processor which, in some example arrangements, can execute instructions stored, or otherwise accessed, via different areas of memory). Alternatively, or additionally, the one or more processors can be structured to perform or otherwise execute certain operations independent of one or more co-processors. In other example arrangements, two or more processors can be coupled via a bus to enable independent, parallel, pipelined, or multi-threaded instruction execution. Each processor can be implemented as one or more general-purpose processors, ASICs, FPGAs, DSPs, or other suitable electronic data processing components structured to execute instructions provided by memory. The one or more processors can take the form of a single core processor, multi-core processor (e.g., a dual core processor, triple core processor, quad core processor, etc.), microprocessor, etc. In some arrangements, the one or more processors can be external to the apparatus, for example, the one or more processors can be a remote processor (e.g., a cloud-based processor). Alternatively, or additionally, the one or more processors can be internal and/or local to the apparatus. In this regard, a given circuit or components thereof can be disposed locally (e.g., as part of a local server, a local computing system, etc.) or remotely (e.g., as part of a remote server such as a cloud-based server). To that end, a circuit, as described herein can include components that are distributed across one or more locations.

The circuit can also include electronics for emitting and receiving acoustic energy such as a power amplifier, a receiver, a low noise amplifier or other transmitter receiver components. In some embodiments, the electronics are an ultrasound system. In some embodiments, the system is comprised of a headset which is used to adjust the position of a probe such as a TCD ultrasound probe. The headset can be configured manually or use an automated robotic system to position the probe over a desired location on the head. The probe transmits and receives acoustic energy which is controlled by an electronic circuit. The electronic circuit has an analog circuit component such as a power amplifier which sends a signal to the probe. The probe than receives the signal which is amplified by an analog low noise amplifier either within the probe or in the analog circuit. Both the transmitted and received signals may be digitized by the circuit. In some embodiments, the send and receive chain may be made up of entirely digital components.

An example system for implementing the overall system or portions of the arrangements can include a general-purpose computer, including a processing unit, a system memory, and a system bus that couples various system components including the system memory to the processing unit. Each memory device can include non-transient volatile storage media, non-volatile storage media, non-transitory storage media (e.g., one or more volatile and/or non-volatile memories), etc. In some arrangements, the non-volatile media may take the form of ROM, flash memory (e.g., flash memory such as NAND, 3D NAND, NOR, 3D NOR, etc.), Electrically Erasable Programmable Read-Only Memory (EEPROM), Magnetoresistive Random Access Memory (MRAM), magnetic storage, hard discs, optical discs, etc. In other arrangements, the volatile storage media can take the form of RAM, Thyristor Random Access Memory (TRAM), Z-Capacitor Random Access Memory (ZRAM), etc. Combinations of the above are also included within the scope of machine-readable media. In this regard, machine-executable instructions comprise, for example, instructions and data which cause a general-purpose computer, special purpose computer, or special purpose processing machines to perform a certain function or group of functions. Each respective memory device can be operable to maintain or otherwise store information relating to the operations performed by one or more associated circuits, including processor instructions and related data (e.g., database components, object code components, script components, etc.), in accordance with the example arrangements described herein.

The controller 130 further includes a signal processing circuit 238, which can be implemented with the processing circuit 232 or another dedicated processing circuit. The signal processing circuit 238 receives the ultrasound data from the headset device 110 and generates the CBFV waveforms in the manner described. The signal processing circuit 238 can further determine the morphology indicators for the CBFV waveforms or the average thereof. The signal processing circuit 238 can configure the output device 140 to display the CBFV waveforms, the average thereof, and the morphology indicators.

The controller 130 further includes a robotic control circuit 240, which can be implemented with the processing circuit 232 or another dedicated processing circuit. The robotic control circuit 240 is configured to control the robotics 214 based on the morphology of the CBFV waveforms during the operation of the visualization system 100 in the manner described. In particular, the robotic control circuit 240 is configured to control the positioning of the probe 105 using information regarding the morphology of the waveforms.

Figure 3:
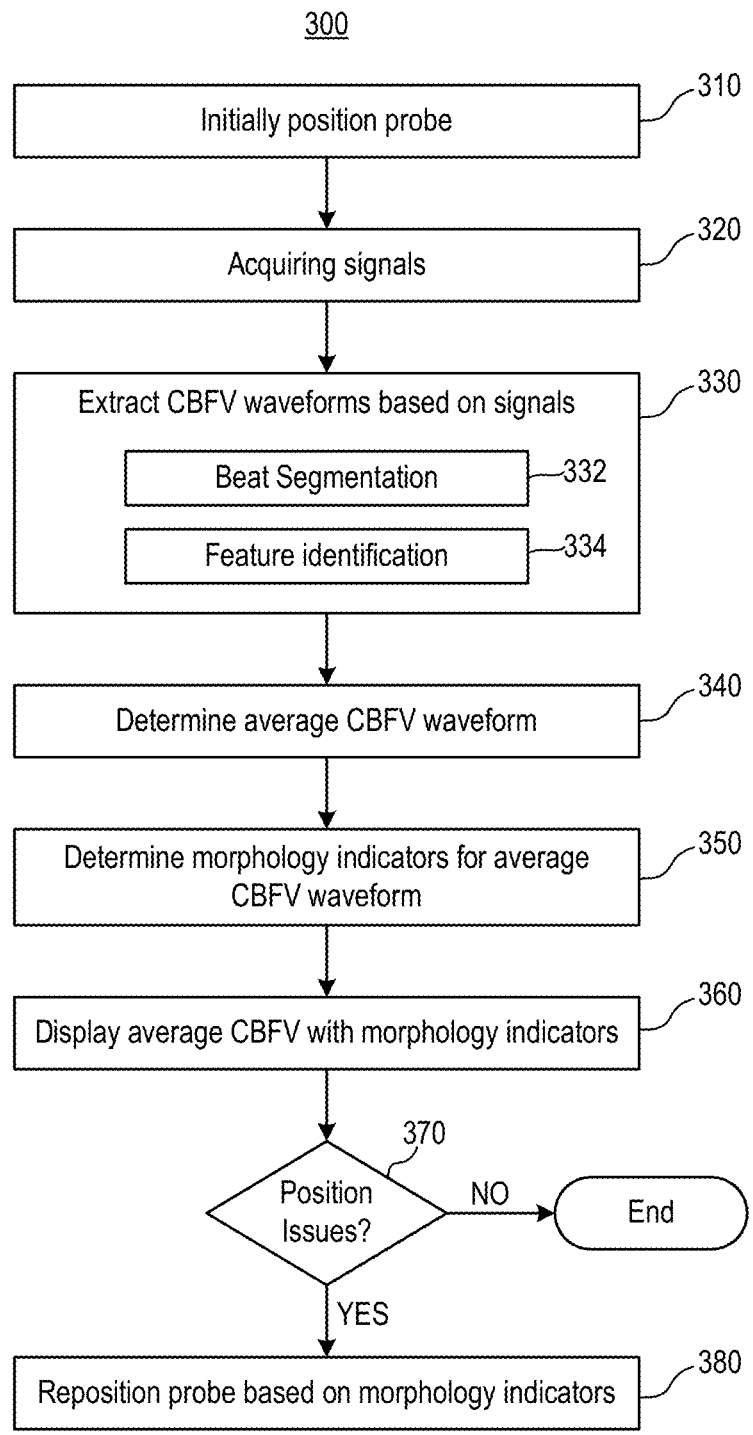
FIG. 3 is a processing flow diagram illustrating a method for facilitating medical diagnosis using the waveform visualization system (FIG. 1) according to various arrangements.

FIG. 3 is a processing flow diagram illustrating a method 300 for facilitating medical diagnosis using the waveform visualization system 100 (FIG. 1) according to various arrangements. Referring to FIGS. 1-3, at 310, the robotics 214 can initially position the probe 105 and/or the headset device 110 in a setup phase, before signal acquisition is performed. The robotics 214 represent a kinematic mechanism that positions the transducer of the probe 105 at an acoustic window (e.g., the temporal window region) adjacent to the head 102. The robotics 214 can automatically position the probe 105 based on prior knowledge of the human anatomy and cerebral hemodynamics in some arrangements. In some arrangements, the robotics 214 can initially position the probe 105 based on user input received by the input device 250. In some arrangements, a human operator can physically position the probe 105 at the acoustic window.

At 320, the headset device 110 (e.g., the probe) acquires signals (e.g., ultrasound data) during an operation phase. The ultrasound data is indicative of CBFV. The signals are streamed, via the network 120, to the controller 130 for processing.

At 330, the signal processing circuit 238 is configured to extract CBFV waveforms based on the signals. The streamed data can be processed and plotted (e.g., CBFV versus time) to generate a continuous CBFV output (which can be displayed in the manner described with respect to a CBFV output diagram 420 of FIG. 4). Extracting the CBFV waveforms refers to dividing the continuous CBFV into multiple CBFV waveforms, each of which corresponds to a pulse or a heartbeat. Using the continuous CBFV output as a starting point, the signal processing circuit 238 can extract the CBFV waveforms associated with the continuous CBFV output. In some examples, extracting the CBFV waveforms can be performed using a method 800 shown in FIG. 8. In another example, determining the CBFV waveforms can be performed by performing heartbeat or pulse segmentation 332 and feature (morphology attribute) identification 334. Examples of the manner in which the signal processing circuit 238 determines the CBFV waveforms, including heartbeat or pulse segmentation 332 and feature (morphology attribute) identification 334, can be found in non-provisional patent application Ser. No. 15/399,710, titled SYSTEMS AND METHODS FOR DETERMINING CLINICAL INDICATIONS, and filed on Jan. 5, 2017, which is incorporated herein by reference in its entirety.

At 340, the signal processing circuit 238 is configured to determine a derived (e.g., average) CBFV waveform. The average CBFV waveform is an average (e.g., mean or median) of the CBFV waveforms in a predetermined time interval. For example, the average CBFV waveform may be a moving average or a moving mean of the CBFV waveforms in a predetermined time interval. The CBFV waveforms are determined per 330. The CBFV waveforms determined per 330 may be filtered to remove noise, before the CBFV waveforms are averaged. One of ordinary skill in the art appreciates that filtering and averaging described herein are examples of how the derived or average CBFV can be derived from the CBFV waveforms determined per 330. The predetermined time interval can correspond to the periodic refresh rate of the CBFV output as presented by the output device 140. The predetermined time interval and/or the refresh rate of the CBFV output can depend on the heartrate of the patient 101, display screen size, processing latency/delay, user settings, and the like. An example of the periodic refresh rate is a periodic refresh rate of a first window 410 of FIG. 4. The predetermined time interval can be determined in other suitable manners.

At 350, the signal processing circuit 238 determines morphology indicators for the derived (e.g., average) CBFV waveform. The morphology indicators correspond to morphological attributes of the average CBFV waveform. Thus, determining the morphology indicators includes determining the morphological attributes of the average CBFV waveform. In some arrangements, given that the average CBFV waveform is an average of the CBFV waveforms within the predetermined time interval, the morphological attributes of the average CBFV waveform can be an average of corresponding morphological attributes of the CBFV waveforms within the predetermined time interval. For example, a first characteristic peak of an average CBFV waveform may have an x-coordinate equal to an average (e.g., mean or median) of time values indicative of when the first characteristic peaks of the CBFV waveforms occur, and a y-coordinate equal to an average of CBFV values (e.g., mean or median) of the first characteristic peaks of the CBFV waveforms. In other arrangements, the morphology attributes of the average CBFV waveform is determined in a manner similar to the manner in which the corresponding morphology attributes of the CBFV waveforms within the predetermined time interval are determined. Alternatively, the time interval may be determined dynamically, for example, based on signal quality. In particular, the better the signal quality (e.g., high signal-to-noise ratio), the shorter the time interval needs to be.

Examples of the morphological attributes include but are not limited to, peaks, valleys, width of peaks, slopes, integrals and the like. The morphology indicators include but are not limited to, dots, lines, highlights, arrows, boxes, brackets, texts, numbers, sounds, tactile feedback, and the like.

At 360, the signal processing circuit 238 configures the output device 140 to display the derived (e.g., average) CBFV with the morphology indicators. Accordingly, the derived CBFV displayed by the output device 140 is analyzed by the controller 130. The morphology indicators (e.g., a dot) can identify a position of a morphological attribute (e.g., a peak) on the average CBFV waveform diagram/graph. The morphology indicators are visual indicators that define a shape or morphology of the average CBFV waveform, thus visually enhancing the average CBFV waveform by visually presenting the extracted physiological data that have been previously ignored by care providers. In some arrangements, the signal processing circuit 238 compares the morphology indicators with those of a healthy individual for reference and diagnostic purposes.

Given that the morphology of a CBFV waveform can be quite subtle, and that the morphology can change rapidly within a short period of time, a physician, clinician, technician, or care provider may not be able to identify the morphology or may not have the time to do so. With the morphological indicators, the physician, clinician, technician, or care provider can immediately understand the morphology of a CBFV waveform and the medical considerations associated therewith. Diagnosis of the patient 101 in real-time or semi-real-time can be achieved as the morphology indicators are displayed. As such, the morphology indicators can assist in diagnosing and treating the patient 101 by presenting useful information to the operator or by automatically identifying issues corresponding to the morphology attributes.

Beyond displaying of morphology indicators, the signal processing circuit 238 can automatically detect medical conditions or can diagnose the patient 101 using the morphology indicators/attributes. Machine learning can be implemented to use heuristic data of known medical conditions and associated CBFV waveforms (or changes thereof over time) as learning examples. Based on such learning examples, morphology attributes of interest (e.g., peaks, valleys, width of the peaks, or other defined or undefined morphology attributes) can be extracted as representative criteria due to the correlation with a certain medical condition. Various categories can be created, including but are not limited to, normal, medical condition type A, medical condition type B, . . . , and medical condition type N. A database (not shown) stores the categories and the morphology indicators/attributes associated therewith. To identify a medical condition that the patient 101 is experiencing, the signal processing circuit 238 can implement a classifier to classify the average CBFV waveform, the morphological attributes, and/or changes thereof over time into one of the various categories. An example of the classifier is a kernel-based classifier, such as but not limited to a support vector machine (SVM) and spectral regression kernel discriminant analysis (SR-KDA).

The signal processing circuit 238 can configure the output device 140 to initiate visual display, audio output, or tactile feedback to notify the operator of the medical condition automatically detected based on the morphology indicators/attributes. The signal processing circuit 238 can configure the network interface 260 to send an email, a page, an SMS message, or call the operator to notify the operator of the detected medical condition. For example, the signal processing circuit 238 can configure the network interface 260 to notify the operator at Electronic Health Record (HER) interfaces, patient monitors, patient alarms, and the like. This is can be extremely useful in a continuous monitoring scenario in which the patient 101 is continuously monitored for medical conditions (e.g., increased ICP) and a care provider may not be present all the time. Such automated diagnosis based on CBFV waveforms were not implemented conventionally, nor does an operator interpret the waveform in the manner described in real-time or semi-real time. Therefore, such arrangements improve the field of medical diagnosis by automating a process that is not previously automated.

Moreover, the waveform visualization system 100 can include or otherwise operatively coupled to other medical devices capable of actuating medical operations automatically based on the medical conditions automatically detected based on the morphology indicators/attributes. For example, responsive to determining that the patient 101 is experiencing increased ICP, the signal processing circuit 238 can configure the network interface 260 to send a command to an intravenous (IV) injection machine or device to automatically administer a drug (e.g., Mannitol, Acetazolamife, and the like) of a suitable dosage to treat the increased ICP. In some examples, the dosage depends on the amount of ICP increased. The amount of ICP increased and the corresponding dosage can also be determined based on machine learning.

In some arrangements, responsive to determining that a point on the waveform or a difference between two points on the waveform are below or above a threshold, ultrasound beam emitted from the probe 105 can be adjusted by the signal processing circuit 238. The adjustments can include but are not limited to, adjusting measurement depth, adjusting beam power, adjusting sample size or volume, and adjusting measurement time. For example, responsive to determining that one or more of the peaks 510*a*, 520*a*, or 530*a* are below a first threshold or responsive to determining that a difference between two or more of the peaks 510*a*, 520*a*, or 530*a* are below a threshold, the signal processing circuit 238 can perform one or more of increasing beam power, increasing sample size, and increasing measurement time. On the other hand, responsive to determining that one or more of the peaks 510*a*, 520*a*, or 530*a* being above a second threshold, the signal processing circuit 238 can perform one or more of decreasing beam power, decreasing sample size, or decreasing measurement time. The first and second thresholds can be defined using machine learning. Machine learning can be implemented to use heuristic data of known ultrasound beam characteristics (including but not limited to, measurement depth, beam power, sample size or volume, and measurement time) and associated CBFV waveforms (or changes thereof over time) as learning examples. Based on such learning examples, morphology attributes of interest (e.g., peaks, valleys, width of the peaks, or other defined or undefined morphology attributes) can be extracted as the first and second thresholds. A database (not shown) stores the thresholds and the morphology indicators/attributes associated therewith.

In addition, the morphology indicators can assist in equipment calibration and test setup, including repositioning of the headset device 110 and/or the probe 105 to improve data accuracy. By reviewing the morphology indicators, a physician, clinician, technician, or care provider can determine equipment misalignment or setup issues/inaccuracies.

An operator can perform actions such as but not limited to, adjusting a tilt of tilt table, adjusting the probe 105 on the head 102, and applying more gel on the head 102. In some examples, the operator can use the input device 250 to define parameters based on which the robotics 214 can translate the probe 105 along a surface of the head 102 and to move the probe 105 with respect to (e.g., toward and away from) the head 102.

Furthermore, equipment calibration or test setup can be performed automatically using the robotic control circuit 240 and the robotics 214. For instance, at 370, the signal processing circuit 238 determines whether there is a position issue with respect to the probe 105 based on the morphology attributes/indicators. For instance, certain morphology attributes/indicators or changes to the morphology attributes/indicators over time correspond to particular misalignment of the headset device 110 and/or the probe 105 with the head 102, or a lack of gel to improve transmission. In some examples, responsive to determining that a point (e.g., the peaks 510*a*, 520*a*, or 530*a*) on the waveform or responsive to determining that a difference between two points (e.g., two of the peaks 510*a*, 520*a*, or 530*a*) on the waveform are below or above a threshold, a position issue or a lack of gel is detected.

Machine learning can be likewise implemented to use heuristic data of known misalignment types and associated CBFV waveforms (or changes thereof over time) as learning examples. Based on such learning examples, morphology attributes of interest (e.g., peaks, valleys, width of the peaks, and the like) can be extracted as representative criteria due to the correlation with a certain type of misalignment. Various categories can be created, including but are not limited to, no misalignment issue, misalignment issue type A, misalignment issue type B, . . . , and misalignment issue type N. The categories can be defined with respect to physical attributes of the patient 101, which include parameters or ranges for an age, gender, weight, head size, preexisting medical conditions, and the like. This provides further granularity in defining the categories. A database (not shown) stores the categories, the physical attributes associated therewith, and the morphology indicators/attributes associated therewith in the form of templates. An operator can use the input device 250 to define the physical attributes of the patient 101. Based on those parameters or ranges, a template associated therewith can be retrieved and compared with the morphology of the waveform. To determine whether a misalignment has occurred, the signal processing circuit 238 can implement a classifier to classify the average CBFV waveform, the morphological attributes, and/or changes thereof over time into one of the various categories associated with the physical attributes of the patient 101.

Responsive to determining that there are no position issues (370:NO), the method 300 ends. On the other hand, responsive to determining that there is a position issue (370:YES), the robotic control circuit 240 configures the robotics 214 to reposition the probe 105 based on the morphology indicators/attributes, at 380.

In some arrangements, either displaying the morphology indicators (360) or automatically adjusting the probe 105 (370 and 380) is performed. In other arrangements, both displaying the morphology indicators and automatically adjusting the probe 105 are performed in any suitable sequence or simultaneously.

Figure 4:
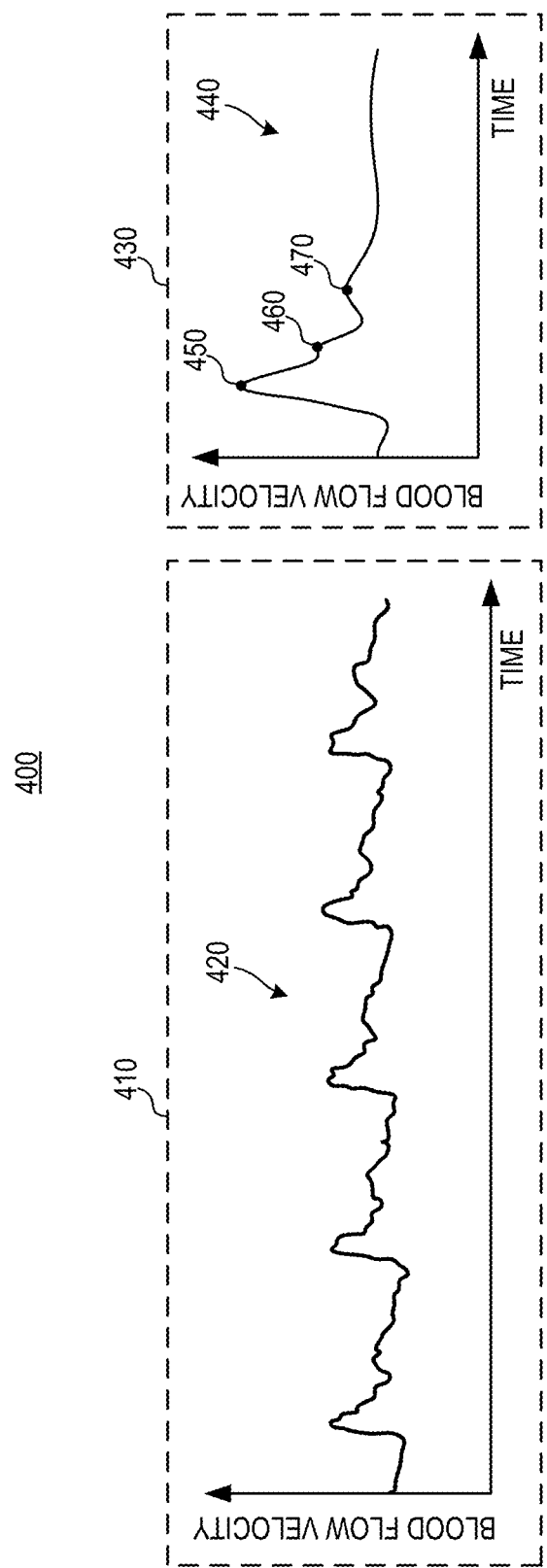
FIG. 4 is a display interface showing a CBFV output diagram and a CBFV waveform diagram of the patient (FIG. 1) according to various arrangements.

FIG. 4 is a display interface 400 showing a CBFV output diagram 420 and a CBFV waveform diagram 440 of the patient 101 (FIG. 1) according to one example. Referring to FIGS. 1-4, the display interface 400 is an example of an interface displayed by the output device 140 at 360. The output device 140 displays the CBFV output diagram 420 in a first window 410 of the display interface 400. The output device 140 displays the CBFV waveform diagram 440 in a second window 430 of the display interface 400. The second window 430 can be referred to as a morphology display window. The vertical axes in the diagrams 420 and 440 correspond to blood flow velocity (in cm/s or cm/ms), and the horizontal axes in the diagrams 420 and 440 correspond to time (in s or ms). The CBFV output diagram 420 can be displayed in real-time or semi-real time as the signals (e.g., ultrasound data) are collected at 320. Displaying of the CBFV output diagram 420 may be delayed due to signal processing. Some methods of heartbeat or pulse segmentation 332 and feature (morphology attribute) identification 334 may not be used in real-time with streaming data as future knowledge of the signals are needed for more accurate processing. Accordingly, in some arrangements, the controller 130 introduces a reporting latency. The CBFV output diagram 420 is continuously updated or periodically updated as new signals are collected at 320.

As shown, the CBFV output diagram 420 visually presents multiple continuous CBFV waveforms for a given time interval as determined at 330. The CBFV output is pulsatile, driven by the cardiac cycle of the patient 101. The CBFV output appears to be periodic in nature, with each distinct CBFV waveform (each period) corresponding to a pulse or heartbeat. The CBFV waveforms shown in the diagram 420 appear to have morphological features such as but not limited to peaks and valleys. However, given the irregularities of the CBFV output and that the CBFV output diagram 420 is constantly updated to account for new data, it is difficult to diagnose based on the CBFV output diagram 420 without assistance from visual indicators that visually identify and emphasize the morphological features to allow an operator to perceive what the CBFV waveforms mean immediately.

The CBFV waveform diagram 440 displays the derived (e.g., average) CBFV waveform determined at 340. The average CBFV waveform is the average of the multiple waveforms displayed in the CBFV output diagram 420. By displaying an average CBFV waveform, negative effects, such as but not limited to, noise and fluctuation in the raw signals acquired at 320 can be reduced. The CBFV waveform diagram 440 can also display an average CBFV waveform that has been graphically processed (such as but not limited to, smoothed, enlarged, and scaled) to emphasize certain morphology features. In other arrangements, the CBFV waveform diagram 440 displays a waveform selected by the signal processing circuit 238 from multiple waveforms captured for the predetermined period of time.

In some arrangements, the CBFV waveform diagram 440 displays the derived (e.g., average) CBFV waveform with at least one previous average CBFV waveform, all superimposed on each other in a same diagram or displayed adjacent to each other to illustrate changes of the average CBFV waveforms over time. In an example in which the CBFV output diagram 420 is updated periodically such that an average CBFV waveform is determined for each period, each of the at least one previous average CBFV waveform corresponds to a previous period that is no longer displayed.

In some arrangements, the CBFV waveform diagram 440 displays the derived (e.g., average) CBFV waveform with at least one of the CBFV waveforms displayed in the CBFV output diagram 420, superimposed on each other in a same diagram or displayed adjacent to each other. In some arrangements, the CBFV waveform diagram 440 displays two or more CBFV waveforms displayed in the CBFV output diagram 420 (without displaying the derived CBFV), all superimposed on each other in a same diagram or displayed adjacent to each other. Aligning any CBFV waveforms can be achieve due to beat segmentation, which identifies a starting point and an end point of a particular CBFV waveform.

In the arrangements in which the CBFV waveform diagram 440 displays multiple CBFV waveforms, the morphology indicators for one of the CBFV waveforms are displayed to avoid visual crowding and confusion. In other arrangements, the morphology indicators for two or more of the CBFV waveforms are displayed.

Figure 5A:
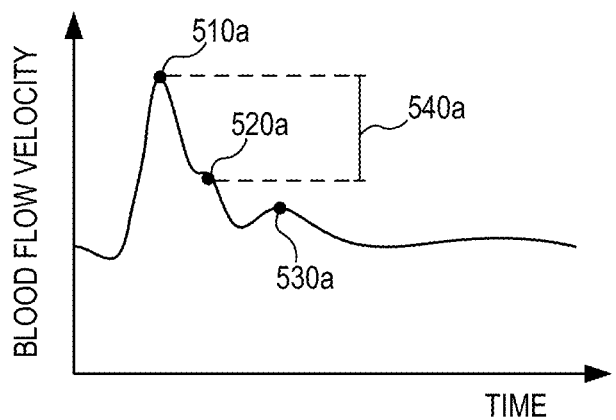
FIG. 5A is a CBFV waveform diagram of a healthy individual according to various arrangements.
Figure 5B:
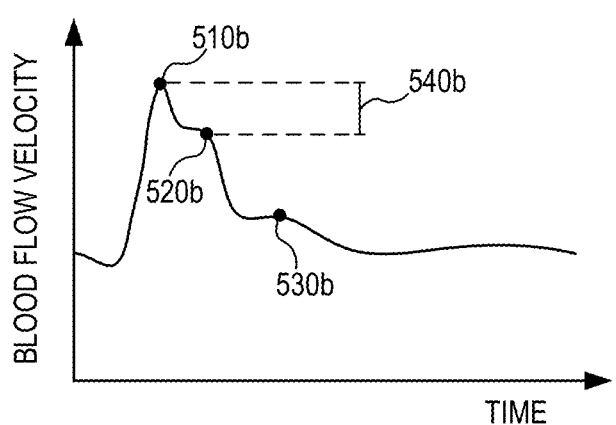
FIG. 5B is a CBFV waveform diagram of a patient suffering from idiopathic intracranial hypertension (IIH) according to various arrangements.

FIGS. 5A and 5B show a non-limiting example of a manner in which morphology or changes in morphology as evidenced by the morphology indicators can be used to detect medical conditions, such as increased ICP. FIG. 5A is a CBFV waveform diagram 500*a* of a healthy individual according to one example. FIG. 5B is a CBFV waveform diagram 500*b* of a patient (of comparable physical characteristics such as gender, age, and race) suffering from idiopathic intracranial hypertension (IIH) according to one example. Referring to FIGS. 1-5B, the vertical axes in the diagrams 500*a* and 500*b* correspond to blood flow velocity (in cm/s or cm/ms), and the horizontal axes in the diagrams 500*a* and 500*b* correspond to time (in s or ms). The diagrams 500*a* and 500*b* may or may not be displayed with an underlying CBFV output diagram (e.g., the CBFV output diagram 420). The CBFV waveforms shown in the diagrams 500*a* and 500*b* can be derived from (e.g., filtered from, an average (mean or median) of, and the like) the underlying CBFV output for a predetermined time interval in the manner described. Alternatively, the CBFV waveforms shown in the diagrams 500*a* and 500*b* can be selected by the signal processing circuit 238 from multiple waveforms captured for the predetermined time interval.

The CBFV waveform diagrams 500*a* and 500*b*, including morphology indicators 510*a*-530*a* and 510*b*-530*b*, can be displayed by the output device 140 to assist a physician, clinician, technician, or care provider with diagnosis, in some arrangement for increased or high ICP. FIGS. 5A and 5B show a case where traditional CBFV metrics such mean velocity, systolic velocity, and diastolic velocity with respect to the CBFV waveform diagrams 500*a* and 500*b* are equal.

As such, the traditional CBFV metrics do not provide insight for diagnosis, however, the morphological indicators might.

In the CBFV waveform diagram 500a, a second characteristic peak (visually identified by the morphology indicator 520a) is a first distance away from a first characteristic peak (visually identified by the morphology indicator 510a). In the CBFV waveform diagram 500b, a second characteristic peak (visually identified by the morphology indicator 520b) is a second distance away from a first characteristic peak (visually identified by the morphology indicator 510b). The second distance is considerably shorter than the first distance. The distance between the first characteristic peak and the second characteristic peak can be used to determine increased or high ICP, given that the distance between the first characteristic peak and the second characteristic peak can correlate with ICP. Specifically, shorter distance between the first characteristic peak and the second characteristic peak is typically associated with higher ICP.

As such, by displaying the morphology indicators 510a-530a and 510b-530b, a physician, clinician, technician, or care provider can immediately perceive the relationships between morphology of the CBFV waveforms shown in the diagrams 500a and 500b in real-time, as such, measurements are taking place, to diagnose the patient and to take actions. In some arrangements, these measurements are from two different people at two different times. It may be possible to used stored, normative data of that range and compare it. It also may be possible to compare waveforms from two sides. Or, it may be possible to compare to stored waveforms of that subject. To further notify an operator of the morphology of the CBFV waveforms shown in the diagrams 500a and 500b, additional morphology indicators 540a and 540b can be used to visually emphasis the first distance and the second distance, respectively. Other forms of visual or audio notifications, warnings, or tactile feedback can be provided if the distance between the first characteristic peak and the second characteristic peak falls below a predetermined threshold. The predetermined threshold can be an absolute length (e.g., in cm) or a percentage (e.g., a 5%, 10%, 15%, 20%, or the like of the blood flow velocity of the first characteristic peak or of the second characteristic peak). In other examples, the predetermined threshold corresponds to the value of the second characteristic peak exceeding the value of the first characteristic peak.

FIGS. 5A and 5B show an exemplary connection between specific CBFV waveform morphology attributes and ICP. One of ordinary skill in the art can appreciate that other connections between CBFV waveform morphology attributes and other medical conditions exist and can be likewise visually presented (e.g., identified or highlighted by morphology indicators) to assist a physician, clinician, technician, or care provider with diagnosis of those medical conditions. To name a few, CBFV waveform morphology attributes are linked to vasodilatation, vasoconstriction, capillary bed expansion, and the like.

While FIGS. 4-5B show morphology indicators 450-470, 510a-530a, and 510b-530b that correspond to peaks, one of ordinary skill in the art can appreciate that morphology indicators corresponding to other morphological features (e.g., valleys, slopes at peaks, slopes at valleys, width of a peak, and the like) of the CBFV waveforms can be likewise displayed. Such morphology indicators/attributes can be likewise implemented for machine learning.

With respect to stroke analysis, a trained operator typically examines dampened signal, blunted signal, minimal signal, or absent signal of a CBFV waveform to detect stroke. This relies on an operator's skill and interpretation, which is subjective. The dampened signal, blunted signal, minimal signal, and absent signal also correspond to an overall feel of the CBFV waveform and does not relate to particular morphological attributes. Arrangements disclosed herein relate to graphically presenting the morphological attributes using suitable indicators to assist an operator in detecting and analyzing stroke. Additional arrangements allow automated detection of stroke, a CBFV waveform-based process that had not been previously automated.

Figure 5C:
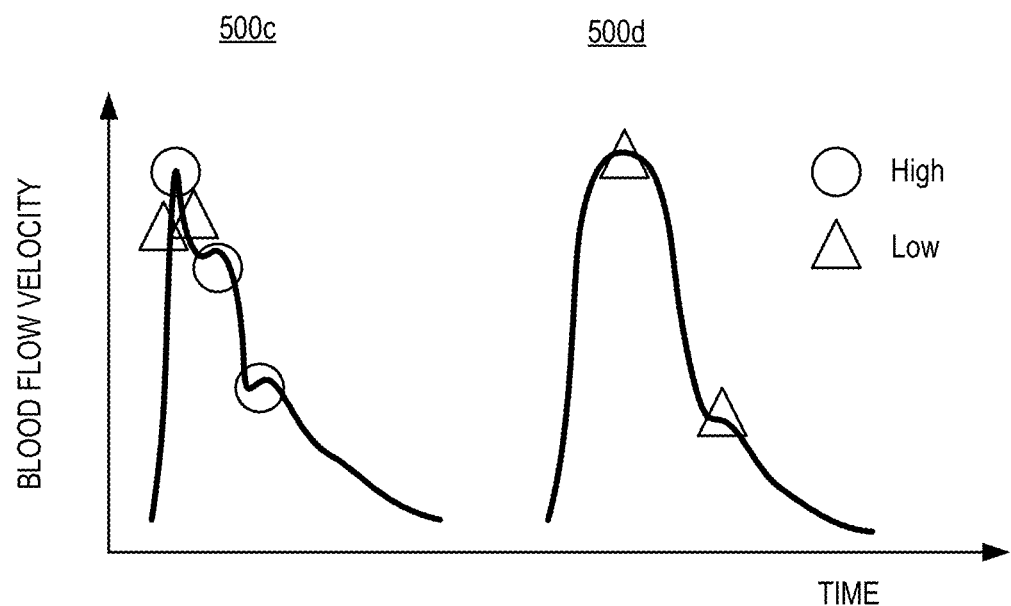
FIG. 5C is a CBFV waveform diagram of a healthy individual (left) and a CBFV waveform diagram of a patient suffering from LVO (right) according to various arrangements.

FIG. 5C is a CBFV waveform diagram 500c of a healthy individual (left) and a CBFV waveform diagram 500d of a patient suffering from LVO (right) according to one example. FIG. 5C shows non-limiting examples of a manner in which morphology or changes in morphology as evidenced by the morphology indicators can be used to detect medical conditions, such as LVO. Referring to FIGS. 1-5C, the vertical axes in the diagrams 500c and 500d correspond to blood flow velocity (in cm/s or cm/ms), and the horizontal axes in the diagrams 500c and 500d correspond to time (in s or ms). The diagrams 500c and 500d may be displayed by the output device 140. The diagrams 500c and 500d may be displayed with an underlying CBFV output diagram (e.g., the CBFV output diagram 420). The CBFV waveforms shown in the diagrams 500c and 500d can be derived from (e.g., filtered from, an average (mean or median) of, and the like) the underlying CBFV output for a predetermined time interval in the manner described. Alternatively, the CBFV waveforms shown in the diagrams 500c and 500d can be selected by the signal processing circuit 238 from multiple waveforms captured for the predetermined time interval.

Curvature of a CBFV waveform can be used to diagnose LVO. Curvature is a robust metric for assessing the presence of LVO, conferring various advantages over traditional heuristic procedures. Traditional heuristic procedures require acquisition of CBFV waveforms and power m-mode (PMD) waveforms from multiple vessels in each hemisphere, thus requiring highly trained personnel with advanced anatomical knowledge for data acquisition and analysis. On the other hand, arrangements disclosed herein utilize curvature, which possesses powerful predictive utility even as measured from a single brief recording of MCA flow. This can be significantly enhanced by a paired bilateral recording, regardless of inter-hemispheric depth disparity, and occlusion location. The arrangements can be performed in real-time. The displaying of the morphology indicators (e.g., colors, highlights, pointers, notifications, warnings, and the like) can be easily understood and communicated in real-time by care providers with minimal training.

First, curvature for each waveform can be determined in suitable manners. In a non-limiting example, for an exemplary waveform denoted x(t), below, local curvature (k(t)) can be computed at each time point (t) via the following expression:

$$k(t) = \frac{|x''(t)|}{(1 + x'^2(t))^{\frac{3}{2}}} \quad (1)$$

The signal processing circuit 238 can determine a single curvature metric for each waveform by summing local curvature (e.g., determined using expression (1)) over all time points, including time points associated with a beat "canopy." The beat canopy is defined as a set of time points corresponding to velocities that exceed a given threshold (e.g., 25%) of a total diastolic-systolic range of the waveform. In other words, the beat canopy refers to all time points (t) such that:

$$x(t) \geq x(t_d) + \frac{x(t_s) - x(t_d)}{4},$$

where $t_d$ and $t_s$ represent time points corresponding to a diastolic minimum and a systolic maximum, respectively.

Next, the curvature for each waveform can be graphically presented via the output device 140 using suitable morphology indicators to enable real-time observation and decision-making by care providers. Curvature is a subtle morphology feature often not distinguishable by an operator, especially when the diagrams 500c and 500d are presented in real-time and updated frequently. In the non-limiting example shown in diagrams 500c and 500d, areas of relatively high curvature are denoted with circles while areas with relatively low curvatures are denoted with triangles. As shown, the diagram 500c of a healthy individual shows high curvature, at or approximately close to peaks. On the other hand, the diagram 500d of a patient with LVO exhibits low curvature, even at the peaks.

Machine learning can be implemented to use heuristic data of known medical conditions and associated curvature of CBFV waveforms (or changes of the curvature over time) as learning examples. Based on such learning examples, curvature and associated locations of the curvature can be extracted as representative criteria due to the correlation with a certain medical condition. Various categories can be created, including but are not limited to, normal, medical condition type A, medical condition type B, . . . , and medical condition type N. A database (not shown) stores the categories and the curvature information associated therewith. To identify a medical condition that the patient 101 is experiencing, the signal processing circuit 238 can implement a classifier to classify the curvature information of the CBFV waveform and/or changes thereof over time into one of the various categories.

Figure 6A:
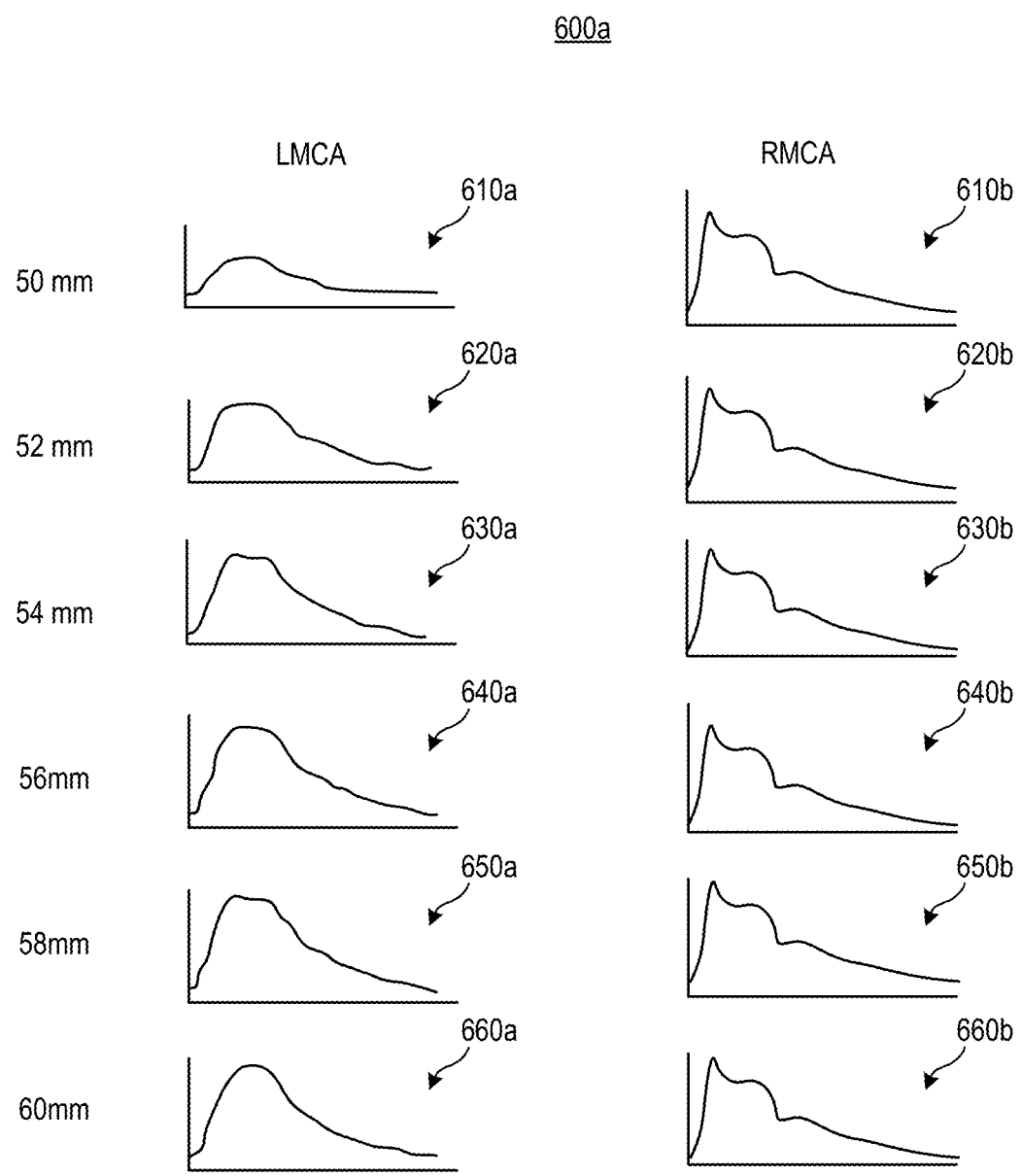
FIG. 6A is a display interface showing CBFV waveform diagrams associated with a left middle cerebral artery (LMCA) of a patient and CBFV waveform diagrams associated with a right middle cerebral artery (RMCA) of the patient according to various arrangements.

FIG. 6A is a display interface 600a showing CBFV waveform diagrams 610a-660a associated with an LMCA of a patient and CBFV waveform diagrams 610b-660b associated with an RMCA of a patient according to one example. Referring to FIGS. 1-6A, the display interface 600a can be displayed by the output device 140. Each of the waveform in the diagrams 610a-660a and 610b-660b can be derived from (e.g., filtered from, an average (mean or median) of, and the like) multiple waveforms in a continuous CBFV output for a predetermined period of time. Each row of diagrams correspond to a particular depth (e.g., 50 mm, 52 mm, . . . , 60 mm) at which the signals are gathered by the probe 105. Thus, for each depth, a CBFV waveform diagram associated with LMCA and another CBFV waveform diagram associated with RMCA are displayed adjacent to one another to allow juxtaposition of similar diagrams. This allows an operator to clearly see the differences between LMCA and RMCA at a particular depth.

The differences can be used to diagnose stroke. In some examples, consistent and significant differences in curvature across the different depths between LMCA and RMCA can be used as an indication of LVO. Consistency can be evaluated on a threshold basis. For example, significant differences above a set threshold number (e.g., 50%, 60%, 75%, and the like) of the depths measured correlates with actual LVO. In the display interface 600a, the left likely has LVO given that with respect to all of the depths measured, the LMCA is associated with a lesser degree of curvature as compared to that of corresponding points or peaks on the RMCA. In some examples, progressive differences between waveforms (e.g., differences between peak values) can be used to determine a depth at which LVO occurs. As shown in the display interface 600a, the difference between corresponding peaks in LMCA and RMCA is most pronounced at 50 mm. This indicates that the LVO is likely occurring at 50 mm. The morphologies (e.g., curvature and peak values) between LMCA and RMCA diverge the greatest at 50 mm as compared to other depths.

Figure 6B:
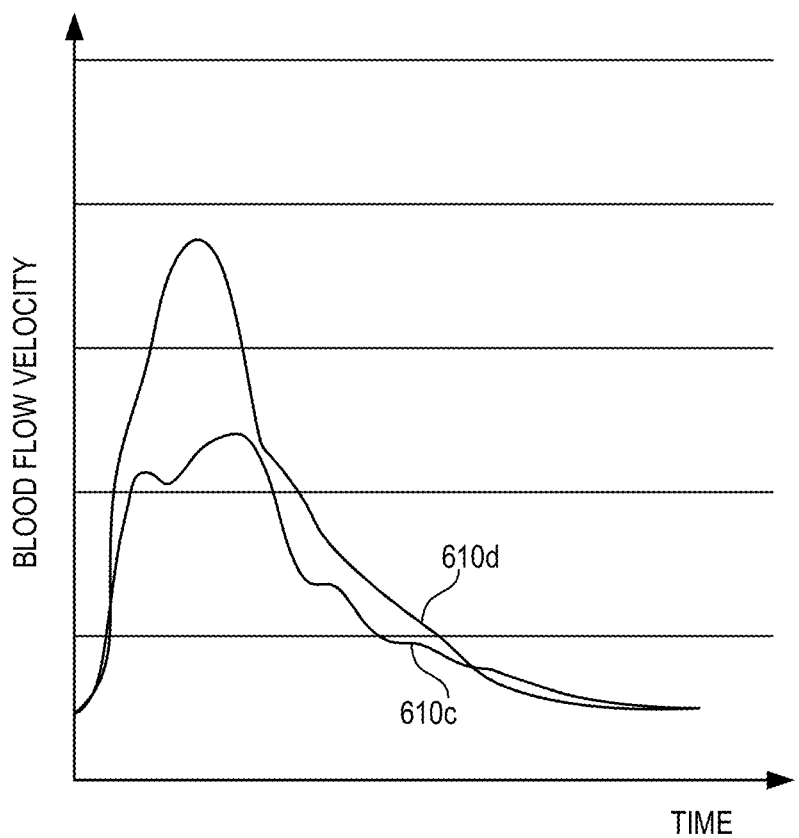
FIG. 6B is a display interface showing a CBFV waveform diagram associated with an LMCA of a patient and a CBFV waveform diagram associated with an RMCA of the patient superimposed on one another according to various arrangements.

FIG. 6B is a display interface 600b showing a CBFV waveform diagram 610c associated with an LMCA of a patient and a CBFV waveform diagram 610d associated with an RMCA of the patient superimposed on one another according to one example. Referring to FIGS. 1-6B, the display interface 600b can be displayed by the output device 140. Each of the waveforms in the diagrams 610c and 610d can be an average (e.g., mean or median) of multiple waveforms in a continuous CBFV output for a predetermined period of time. Instead of displaying the diagrams side-by-side similar to the display interface 600a, the display interface 600b displays the diagrams 610c and 610d in a same diagram, being superimposed on one another. Additional graphical indicators such as colors, arrows, text, and the like can be implemented to distinguish the two plots. For example, the diagrams 610c and 610d can be shown in different colors.

In some arrangements, morphological indicators such as those described herein can be added to the diagrams 610a-660a, 610b-660b, 610c, and 610d.

Figure 6C:
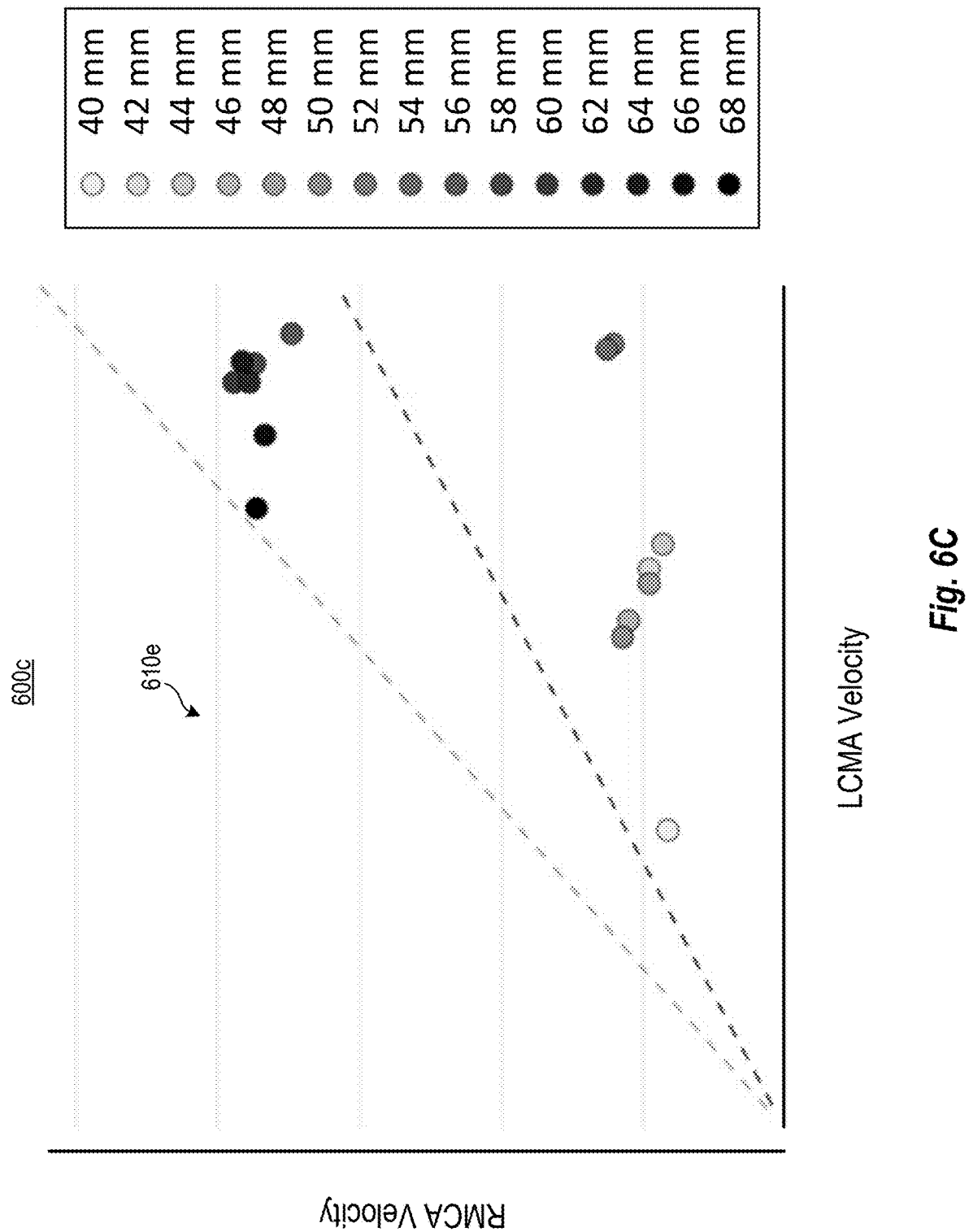
FIG. 6C is a display interface showing an RMCA velocity versus an LMCA velocity diagram associated with a patient according to various arrangements.

FIG. 6C is a display interface 600c showing an RMCA velocity versus LMCA velocity diagram 610e associated with a patient according to one example. Referring to FIGS. 1-6C, the display interface 600c can be displayed by the output device 140. The display interface 600c can be another display interface to organize the underlying data of the interface 600a. Each dot on the diagram 610e represents the RMCA velocity versus the LMCA velocity for a particular depth. The depth can be differentiated by different colors or other visual distinctions such as shapes of the dots. At least one extrapolation line can be used to show trend.

While FIGS. 6A-6C are concerned with comparing RMCA and LMCA, one of ordinary skill in the art can appreciate that the interfaces 600a-600c can be similarly used to juxtapose any two comparable CBFV waveforms, such as one from a healthy individual (control group) with another from a patient with a disease or suspected to have a disease. The two CBFV waveforms can be displayed side-by-side based on depths (similar to interface 600a), superimposed (similar to interface 600b), or have the associated velocities plotted against each other (similar to interface 600c).

Figure 7:
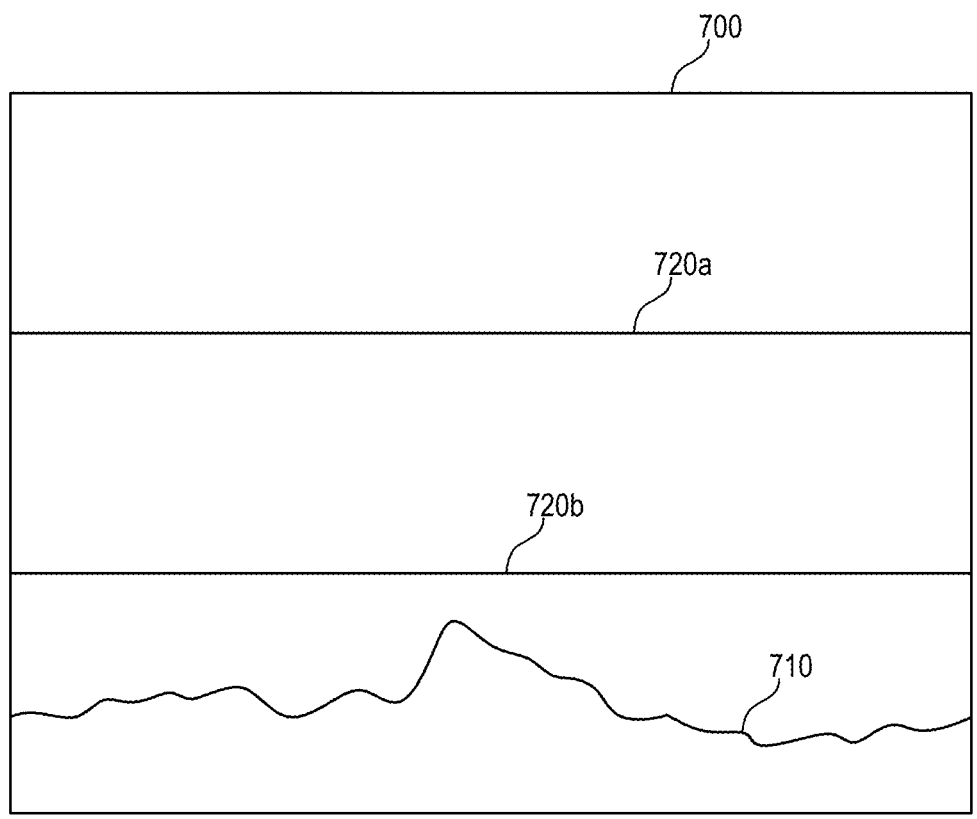
FIG. 7 is a display interface showing a trending window according to various arrangements.

FIG. 7 is a display interface showing a trending window 700 according to one example. Referring to FIGS. 1-7, the trending window 700 can be displayed with one or more other interfaces described herein to provide additional information to assist a physician, clinician, technician, or care provider with diagnosis and/or to adjust the positioning of the headset device 110 and the probe 105. The trending window 700 can be used to trend various parameters related to the CBFV waveforms including but are not limited to, curvature, CBFV, transformations of the CBFV (e.g., those used to emphasize the upslope of a segmented CBFV waveform), SSF of the CBFV, and the like. In particular, the trending window 700 trends a parameter 710. The trending window 700 can include limits 720a and 720b for visual assistance of tracking the parameter 710.

Figure 8:
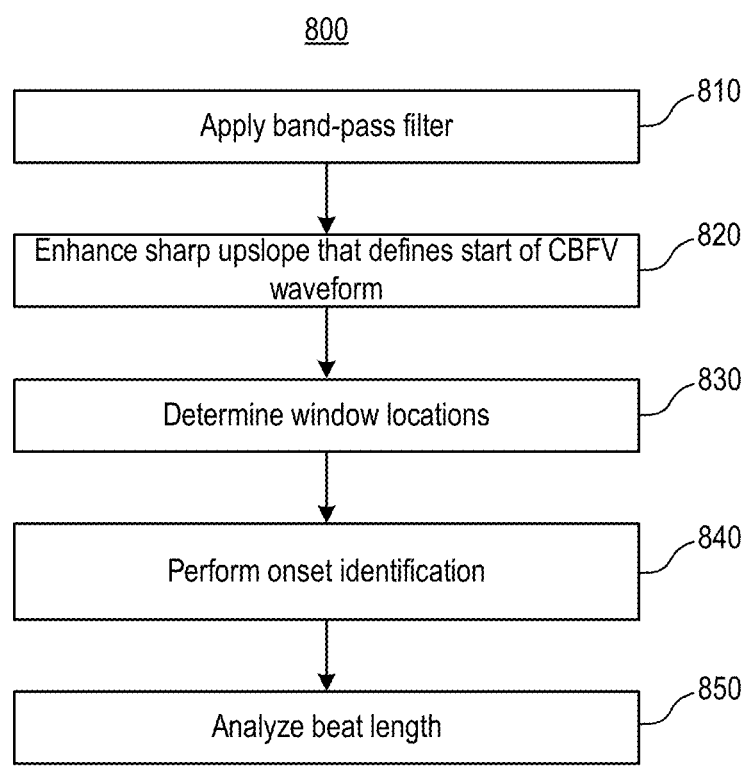
FIG. 8 is a processing flow diagram illustrating a method for extracting CBFV waveforms according to various arrangements.

FIG. 8 is a processing flow diagram illustrating a method 800 for extracting CBFV waveforms according to one example. Referring to FIGS. 1-8, the method 800 can be implemented to extract individual pulses and the CBFV waveforms associated thereof from the continuous signals (continuous CBFV output) acquired at 320. The extracted waveforms can be used as visual diagnosis aides to an operator and/or can be used to adjust positions/orientations of the probe 105 in the manner described. Thus, the CBFV waveform analysis as described herein depends on reliable pulse onset detection. A pulse onset defines a beginning of a pulse or a heartbeat. Accurate CBFV waveform extraction presents a significant challenge for a number of reasons. For one, TCD measurements are affected by signal attenuation due to the skull, thus resulting in a relatively low signal-to-noise ratio. TCD is highly operator-dependent and relies on the operator's ability to locate the acoustic window and to insonate the appropriate vessel within a cerebrovasculature, which varies among individual patients. Additionally, the CBFV signals are particularly prone to noise artifacts as a result of motion of the probe 105 and/or the patient 101. Furthermore, a large variety of possible waveform morphologies can further make CBFV waveform extraction difficult due to lack of predictability. The method 800 addresses such technical issues. In some arrangements, in the absence of any TCD devices or in conjunction with TCD devices, beat start and stop points can be identified using at least another physiological parameter of the heart including but not limited to, Electrocardiogram (EKG), pulse oximetry, heartrate monitors, and the like.

At 810, the signal processing circuit 238 applies a band-pass filter to the signals acquired at 320. In some examples, the band-pass filter is configured to filter out signals outside of a desired range to filter out noise. Examples of the designed range include but are not limited to, 0.5-10 Hz.

At 820, the signal processing circuit 238 enhances at least one sharp upslope that can define a start of a CBFV waveform. In one arrangement, enhancement of the sharp upslope can be achieved by applying a windowed slope sum function (SSF) to the filtered signals generated as a result of 810. The windowed SSF effectively measures a net change in the continuous CBFV output shown in graph 900a over a time interval. A non-limiting example of the SSF ($Z_1$) is:

$$z_i = \sum_{k=i-w}^{i} y_k - y_{k-1} \quad (2)$$

where w is a length of an analyzing window. In addition, $y_k$ and $y_{k-1}$ are adjacent filtered CBFV output signals. In some examples, a length of the analyzing window is equal to, approximately equal to, slightly less than a length of an initial upslope of a typical pulse. Examples of the length of the analyzing window include but are not limited to, 100 ms, 110 ms, 120 ms, 125 ms, 130 ms, and 145 ms. In other arrangements, a difference between a highest point and a lowest point of the CBFV waveform is the net change.

Figure 9:
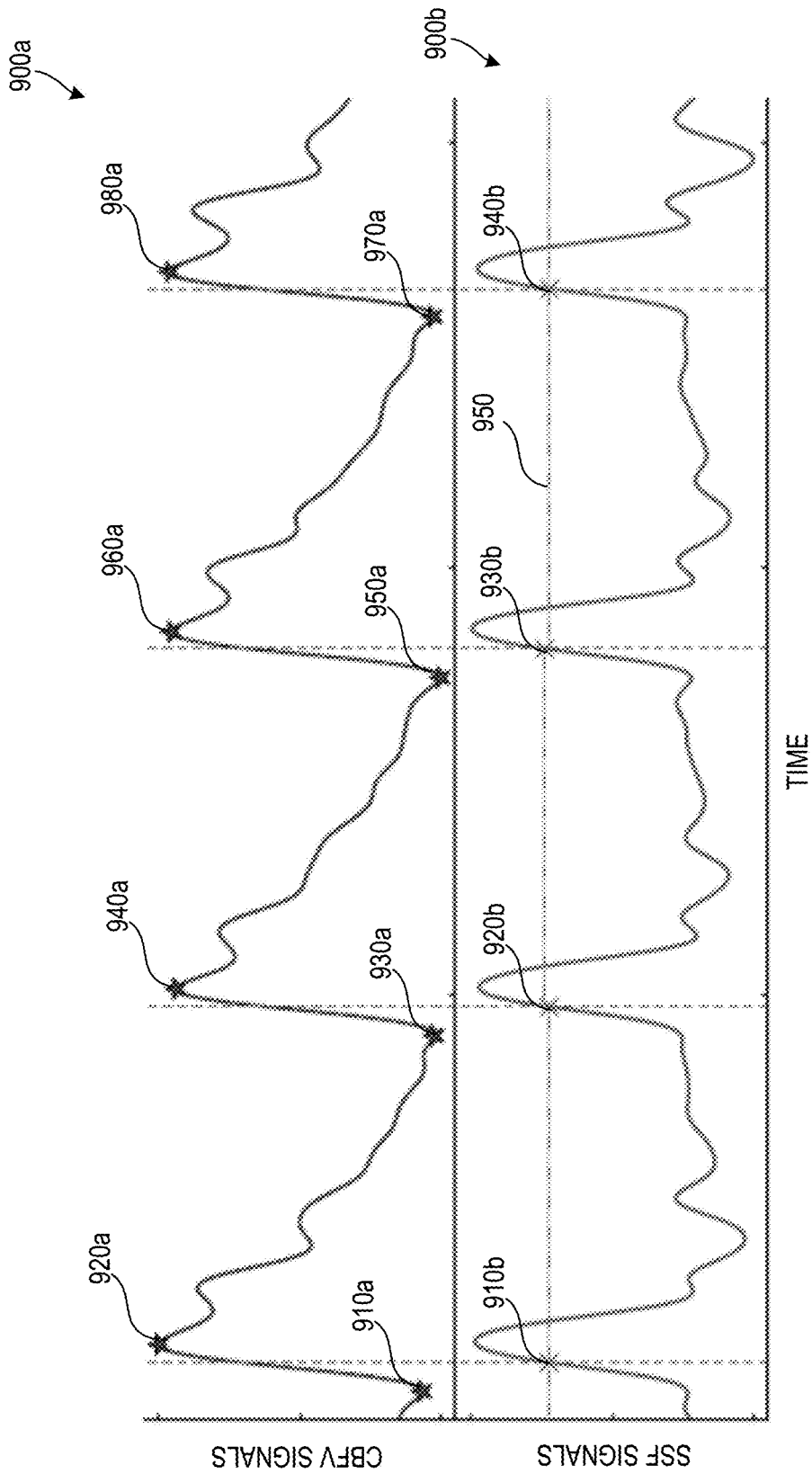
FIG. 9 is a CBFV output diagram showing an example CBFV output and a slope sum function (SSF) corresponding to the CBFV output according to various arrangements.

FIG. 9 is a CBFV output diagram showing an exemplary CBFV output 900a and a SSF signals 900b corresponding to the CBFV output 900a according to one example. Referring to FIGS. 1-9, the CBFV output 900a and the SSF signals 900b are presented in normalized graphs. The CBFV output 900a and the SSF signals 900b are time-aligned. The SSF signals 900b shows the SSF signals corresponding to the signals shown in the CBFV output 900a. The SSF signals 900b can be determined from the signals of the CBFV output 900a using the expression (2) or another suitable method.

At 830, the signal processing circuit 238 determines window locations based on the SSF signals. The window locations define windows in which a pulse onset is likely to occur. To achieve this, the signal processing circuit 238 determines thresholds for the SSF signals. In some examples, the threshold can be established at 60% of an average (mean or median) of a predetermined number (e.g., 10 or a number of peaks identified if the number is less than the predetermined number) of preceding peaks in the SSF signals. A peak is defined as a maximum value of an upslope of a CBFV pulse.

At an initialization phase in which no preceding peaks can be used to establish a threshold, all peaks exceeding a peak threshold are identified by the signal processing circuit 238. An example of the peak threshold is 3 times the average (mean or median) of the SSF signals over a first 10 seconds of the data acquired at 320. The signal processing circuit 238 can set an initial threshold at 60% of an average (mean or median) value of the identified peaks. Responsive to the initial threshold being determined, a threshold line 950 is generated to be horizontally transverse the SSF signals of the CBFV output diagram 900a. Threshold crossing points 910b-940b are points on the diagram 900b that intersect with the threshold line 950. Vertical lines can be generated at the threshold crossing points 910b-940b to be vertically transverse to the diagrams 900a and 900b. A search window is defined as a time interval between a threshold crossing point (e.g., 920b) and a peak (e.g., 920a) of a last-detected pulse immediately preceding a new search window. The new search window can be defined in a manner similar to disclosed with the search window. For a very first onset, the search window is defined as a time interval between a very first threshold crossing point and a beginning of the SSF signals.

In order to avoid locating multiple threshold crossing points immediately adjacent to one another, a refractory period is enforced by the signal processing circuit 238. Within the short refractory period, the signal processing circuit 238 refrains from defining new threshold crossing points. Exemplary lengths of the refractory period include but are not limited to, 150 ms. One of ordinary skill in the art can appreciate that other suitable lengths of the refractory period can be likewise implemented, as long as the refractory period is longer than a pulse upslope time and significantly shorter than an entire pulse length.

The peaks 920a, 940a, 960a, and 980a of each beat should occur close to the threshold crossing points 910b, 920b, 930b and 940b, respectively. In some arrangements, the peaks 920a, 940a, 960a, and 980a are determined by locating a maximum value that occurs within a predetermined time interval (such as but not limited to, about 150 ms) of the corresponding threshold crossing points 910a, 920b, 930b and 940b, respectively. In some arrangements, peak finding can occur as separately from onset locating, responsive to all onsets being located.

At 840, the signal processing circuit 238 performs onset identification. Responsive to a search window being identified, valleys (e.g., 910a, 930a, 950a, and 970a) in the original filtered signals (shown in the diagram 900a) that occur within the search window are identified. A valley that is both closest to a threshold crossing point and satisfies a condition such as but not limited to, $CBFV_{peak} - CBFV_{valley} \geq A(SSF_{peak})$ is designated as a pulse onset.

$CBFV_{peak}$ is a peak value of a CBFV pulse. $CBFV_{valley}$ is the value of the candidate valley. $SSF_{peak}$ is a peak value of the SSF signals for this search window. Factor A is included to avoid falling into valleys that appear in the upslope due to noise artifacts or pathological morphologies. Examples of factor A include but are not limited to, about 0.5, about 0.6, about 0.7, about 0.8, about 0.9, and about 0.5-0.9. Examples of the onsets as shown in diagram 900*b* include the valleys 910*a*, 930*a*, 950*a*, and 970*a*. As such, initial estimates for the waveform onsets are accordingly determined.

At 850, the signal processing circuit 238 analyzes beat length to address outliners. After the output 900*a* has been scanned in its entirety, and the initial onsets are determined per 840, the outliners are addressed based on beat length. The initial processes 810-840 may result in two mistakes, "long beats" and "short beats." Long beats typically occur when a beat is missed, resulting in two beats detected as a single beat. This result may be due to some abnormality in the upslope of the beat, either because the upslope is not sufficiently steep and fails to cross the threshold line (e.g., 950) or because the upslope contains some noise artifacts that suppress the SSF signals. Short beats typically occur as noise causes a sharp upslope based on which a new beat is detected, thus dividing what should be a single beat into two or more shorter beats.

In a non-limiting example, beats are determined to be outliers using a length-based median absolute deviation (MAD) method. For each point in the SSF signals 900*b*, MAD can be computed using the following expression:

$$MAD_i = \text{median}(|X_i - \text{median}(X)|) \quad (3)$$

where X is a univariate data set of the SSF signals 900*b*, having elements $X_i$. Mad can be converted into a proxy for standard deviation by including a scale factor, such as:

$$\hat{\sigma} = B(MAD) \quad (4)$$

where an example of B is about 1.4826. One of ordinary skill in the art can appreciate that other suitable examples of the scale factor B and outliner detection mechanism can be likewise implemented.

In some arrangements, short beats can be defined as beats with a length l that satisfies a condition $l < l_{median} - C(\hat{\sigma}_{length})$. In some arrangements, long beats can be defined as beats with a length l that satisfies a condition $l < l_{median} + C(\hat{\sigma}_{length})$. C is a constant such as but not limited to, about 3.5. C can be any suitable conservative criterion for classifying outliers.

In some arrangements, the signal processing circuit 238 can address the long beats before the short beats. Global beat detection in the manner described with respect to 830-840 can be applied on a smaller scale to address the long beats, with progressively relaxed thresholds. First, a search window is defined with respect to the CBFV signals from the beginning of a peak of an identified long beat to the end of the long beat. The SSF is determined for this segment of CBFV signals. A threshold is set at 60% of the average (mean or median) of all the peaks located in the original global SSF signals during a first pass (e.g., 810-840). The original global SSF signals include the SSF corresponding to the long beat, regular beats, and outer outliner long or short beats. The window locations and onset locations are determined in a same manner as disclosed with respect to 830 and 840, for the SSF signals corresponding to the long beat using such threshold. If new onsets are located, those onset locations are saved. The method proceeds to a next long beat, if any. If no new onsets are located, the threshold (initially at 60%) is incrementally relaxed (decreased). The onset detection is repeated with each iteration associated with relaxed threshold until new onsets are located. For example, for a next iteration, the threshold is set at an increment (e.g., 5%) less than the previous threshold. If no new onsets are found after reducing the threshold value to an increment before the threshold value reaches 0, the long beat is left alone.

Short beats are dealt with after all the long beats have been addressed in some arrangements. The short beats are addressed by viewing each short beat along with its immediate adjacent neighbors to determine whether the short beat should be combined with either of its neighboring beats. If a merger of the short beat with a neighbor beat results in a new beat with a length closer to the average beat length than the original beats, then the merger is performed. In an exemplary arrangement, four lengths related to a short beat are determined: $l_{before}$, $l_{short}$, $l_{after}$, and $l_{median}$. In some examples, $l_{before}$ defines a length of a beat adjacent to and before the short beat. $l_{short}$ defines a length of the short beat itself. $l_{after}$ defines a length of the beat adjacent to and after the short beat. $l_{median}$ is an average (mean or median) beat length of all beats that have been found in the CBFV signals, including beats other than the short beat and its neighbors. A length of a beat is defined to be a time interval between consecutive onsets. The signal processing circuit 238 first checks whether combining $l_{short}$ with $l_{after}$ produces a new beat with a length closer to $l_{median}$ than $l_{after}$. Responsive to determining that the length of the new beat is closer to $l_{median}$, then the beats are combined responsive to determining that a correlation distance between the beats is greater than a threshold, such as but not limited to about 0.1. This is because merging beats involves deleting a beat onset, which should be handled very conservatively. After merging the beats, the method proceeds to a next short beat. If combining $l_{short}$ with $l_{after}$ fails to produce a new beat with a length closer to $l_{median}$ than $l_{after}$ or if the correlation distance between the beats is not greater than the threshold, then the signal processing circuit 238 checks whether combining $l_{short}$ with $l_{before}$ produces a new beat with a length closer to $l_{median}$ than $l_{before}$. Responsive to determining that the length of the new beat is closer to $l_{median}$, and that a correlation distance between the beats is greater than the threshold, the beats are combined. This algorithm can be performed for all short beats until no short beats are remaining.

A single pass often may not address all long and short beats due to the fact that as the beats are added and/or subtracted, statistics (e.g., average peak, $l_{median}$, and the like) may change. Thus, the beat length analysis at 850 ends responsive to determining that no new beats are added and/or subtracted during a single iteration. In some instances, an oscillating solution may be reached, such that a maximum number of iterations (e.g., 10) should be enforced to avoid the ping-pong effect of shifting statistics.

Figure 10:
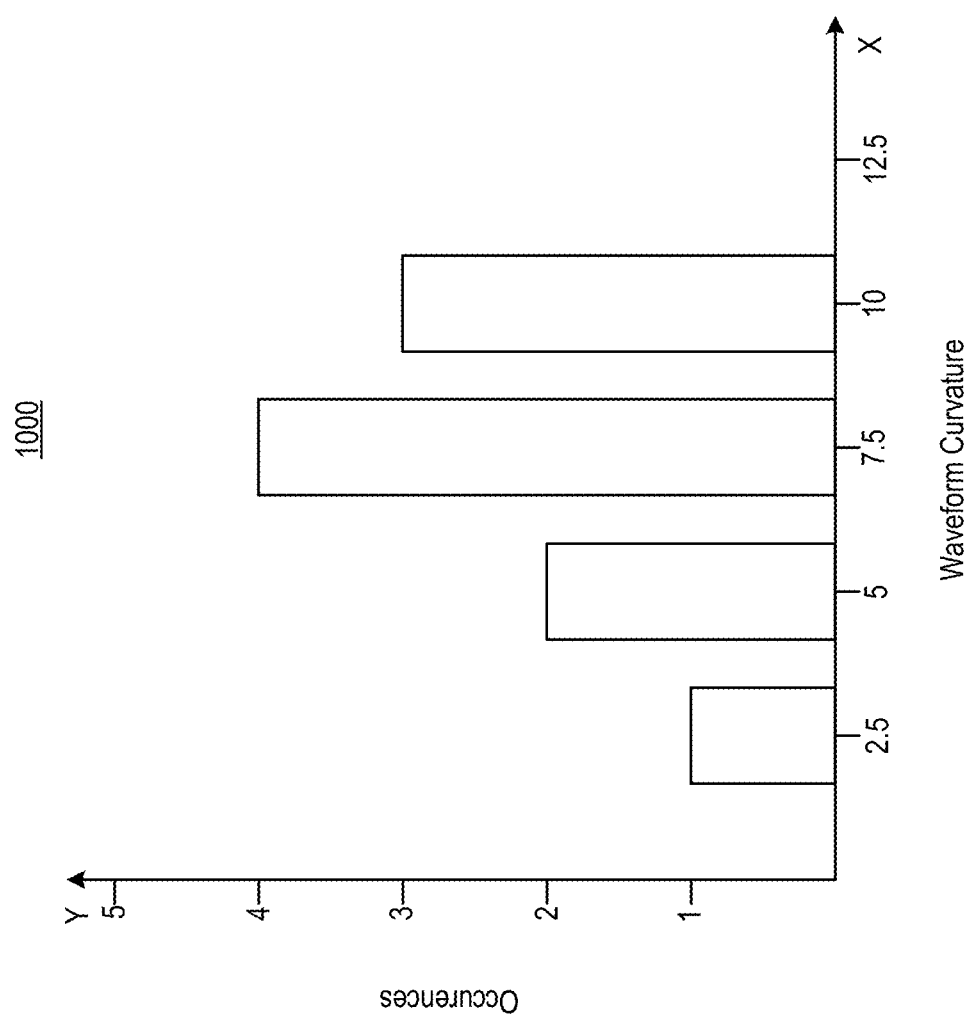
FIG. 10 is a display interface showing an attribute distribution associated with a number of CBFV waveforms according to various arrangements.

In some arrangements, actionable information can be extracted from a distribution of certain attributes of CBFV waveforms. Examples of such attributes include but are not limited to, an average velocity, skew, curvature, kurtosis, and the like of each waveform or of a given peak (e.g., a first peak) of each waveform. Such information can be determined by the controller 130 and displayed on an interface provided by the output device 140. FIG. 10 is a display interface 1000 showing a diagram of an attribute distribution associated with a number of CBFV waveforms according to various arrangements. As shown, an x-axis of the diagram corresponds to an attribute (e.g., curvature) of a first peak of each waveform. A y-axis of the diagram corresponds to a number of occurrences of a particular attribute value (e.g., 2.5, 5, 7.5, 10, 12.5, and the like) among the number of CBFV waveforms. For example, 1 CBFV waveform has a curvature of approximately 2.5, 2 CBFV waveforms have a curvature of approximately 5, 4 CBFV waveforms have a curvature of approximately 7.5, and 3 CBFV waveforms have a curvature of approximately 10.

While curvature is used as a non-limiting example, one of ordinary skill in the art can appreciate other the distribution of other attributes can be similarly graphed. For instance, the x-axis of the graph define values of the attribute while the y-axis of the graph define occurrences of that attribute among the CBFV waveforms or among peaks (e.g., first peaks) of the CBFV waveforms. In addition, the output device 140 can similarly display a distribution of a certain attribute of a given subject being compared (e.g., overlaid) with the distributions of the same attribute of other subjects or with an average distribution across a population (e.g., a general population, a segmented population, and the like).

The above used terms, including "held fast," "mount," "attached," "coupled," "affixed," "connected," "secured," and the like are used interchangeably. In addition, while certain arrangements have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order, and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

The various examples illustrated and described are provided merely as examples to illustrate various features of the claims. However, features shown and described with respect to any given example are not necessarily limited to the associated example and may be used or combined with other examples that are shown and described. Further, the claims are not intended to be limited by any one example.

The foregoing method descriptions and the process flow diagrams are provided merely as illustrative examples and are not intended to require or imply that the steps of various examples must be performed in the order presented. As will be appreciated by one of skill in the art the order of steps in the foregoing examples may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the examples disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the examples disclosed herein may be implemented or performed with a general purpose processor, a DSP, an ASIC, an FPGA or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In some exemplary examples, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in a processor-executable software module which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

The preceding description of the disclosed examples is provided to enable any person skilled in the art to make or use the present disclosure. Various modifications to these examples will be readily apparent to those skilled in the art, and the generic principles defined herein may be applied to some examples without departing from the spirit or scope of the disclosure. Thus, the present disclosure is not intended to be limited to the examples shown herein but is to be accorded the widest scope consistent with the following claims and the principles and novel features disclosed herein.

What is claimed is:

1. A tool for facilitating medical diagnosis, comprising:
    an ultrasound device, wherein the ultrasound device is configured to collect ultrasound data from a patient;
    a processing circuit configured to:
        generate a cerebral blood flow velocity (CBFV) waveform based on the ultrasound data;
        determine morphology attributes of the CBFV waveform, wherein the morphology attributes comprises at least high curvature and low curvature;
        determine two or more morphology indicators that correspond to each of the morphology attributes, wherein the two or more morphology indicators comprise at least a first morphology indicator highlighting the high curvature and a second morphology indicator highlighting the low curvature, wherein the high curvature deviates from being a straight line at a greater rate than the low curvature; and
        determine that the patient is experiencing a medical condition based on the morphology indicators; and
    a display device configured to:
        display the CBFV waveform comprising the morphology attributes;
        highlight the morphology attributes by displaying each of the two or more morphology indicators on or adjacent to a corresponding one of the morphology attributes of the CBFV waveform, wherein the display device is configured to display the CBFV waveform and the two or more morphology indicators as the ultrasound data is being collected, wherein the two or more morphology indicators comprise the first morphology indicator highlighting the high curvature at a first position of the CBFV waveform and the second morphology indicator highlighting the low curvature at a second position of the CBFV waveform, and wherein the first morphology indicator and the second morphology indicator are graphically distinct, and
        display a notification related to the medical condition.

2. The tool of claim 1, wherein the processing circuit generates the CBFV waveform based on the ultrasound data by:
    generating a plurality of CBFV waveforms based on the ultrasound data, each of the plurality of CBFV waveforms corresponding to a pulse; and
    the CBFV waveform used to determine the morphology attributes is derived from the plurality of CBFV waveforms.

3. The tool of claim 2, wherein configuring the display device to display the CBFV waveform and the morphology indicators comprises configuring the display device to display the plurality of CBFV waveforms in a first display window.

4. The tool of claim 3, wherein configuring the display device to display the CBFV waveform and the morphology indicators comprises configuring the display device to display the CBFV waveform and the morphology indicators in a second display window.

5. The tool of claim 2, further comprising deriving the CBFV waveform from the plurality of CBFV waveforms by one or more of filtering the plurality of CBFV waveforms and averaging the plurality of CBFV waveforms.

6. The tool of claim 1, wherein determining the morphology indicators that correspond to each of the morphology attributes of the CBFV waveform comprises:
    segmenting a detected CBFV waveform into distinct CBFV waveforms; and
    identifying the morphology attributes for the CBFV waveform that is an average of the distinct CBFV waveforms.

7. The tool of claim 1, wherein the morphology attributes comprise at least one peak on the CBFV waveform.

8. The tool of claim 7, wherein configuring the display device to display the CBFV waveform and the morphology indicators comprises configuring the display device to display a peak indicator corresponding to each of the at least one peak of the CBFV waveform.

9. The tool of claim 1, wherein the processing circuit is further configured to:
    use machine learning to determine that the patient is experiencing the medical condition.

10. The tool of claim 9, wherein in response to determining that the patient is experiencing the medical condition, the processing circuit is further configured to:
    send an email, a page, or a short message service (SMS) message to an operator;
    call the operator; and/or
    configure a medical device to administer a drug to treat the medical condition.

11. The tool of claim 1, wherein the processing circuit is further configured to:
    determine, based on machine learning, that a probe of the ultrasound device is misaligned based on the morphology indicators; and
    automatically adjust a position of the probe.

12. The tool of claim 1, wherein the first morphology indicator is disposed to contain the first position of the CBFV waveform and the second morphology indicator is disposed to contain the second position of the CBFV waveform.

13. The tool of claim 1, wherein the determining the morphology attributes of the CBFV waveform comprises:
    determining one or more beat canopies within the CBFV waveform;
    determining local curvatures for each time point of the one or more beat canopies;

summing the local curvatures for each of the one or more beat canopies to determine an overall curvature for each of the one or more beat canopies; and determining the beat canopies indicating the high curvature or the low curvature based on the overall curvature.

14. A method for facilitating medical diagnosis, comprising:

collecting, with an ultrasound device, ultrasound data from a patient;

generating a cerebral blood flow velocity (CBFV) waveform based on the ultrasound data;

determining morphology attributes of the CBFV waveform, wherein the morphology attributes comprises at least high curvature and low curvature;

determining two or more morphology indicators that correspond to each of the morphology attributes, wherein the two or more morphology indicators comprise at least a first morphology indicator highlighting the high curvature and a second morphology indicator highlighting the low curvature, wherein the high curvature deviates from being a straight line at a greater rate than the low curvature;

displaying, on a display device, the CBFV waveform comprising the morphology attributes;

highlighting the morphology attributes by displaying each of the two or more morphology indicators on or adjacent to corresponding one of the morphology attributes of the CBFV waveform, wherein the display device is configured to display the CBFV waveform and the two or more morphology indicators as the ultrasound data is being collected, wherein the two or more morphology indicators comprise the first morphology indicator highlighting the high curvature at a first position of the CBFV waveform and the second morphology indicator highlighting the low curvature at a second position of the CBFV waveform, and wherein the first morphology indicator and the second morphology indicator are graphically distinct; and determining, using processing circuitry, that a patient is experiencing a medical condition based on the morphology indicators and configuring the display device to display a notification related to the medical condition.

15. The method of claim 14, wherein determining the morphology indicators identifying the morphology attributes of the CBFV waveform comprises:

segmenting a detected CBFV waveform into distinct CBFV waveforms; and identifying the morphology attributes for the CBFV waveform that is an average of the distinct CBFV waveforms.

16. The method of claim 14, wherein:

the morphology attributes comprise at least one peak on the CBFV waveform; and displaying the CBFV waveform and the morphology indicators comprises displaying a peak indicator corresponding to each of the at least one peak of the CBFV waveform.

17. A non-transitory processor-readable medium storing processor-readable instructions such that, when executed, causes a processor to facilitate medical diagnosis by:

collecting ultrasound data from a patient;

generating a cerebral blood flow velocity (CBFV) waveform based on the ultrasound data;

determining morphology attributes of the CBFV waveform, wherein the morphology attributes comprises at least high curvature and low curvature;

determining two or more morphology indicators that correspond to each of the morphology attributes, wherein the two or more morphology indicators comprise at least a first morphology indicator highlighting the high curvature and a second morphology indicator highlighting the low curvature, wherein the high curvature deviates from being a straight line at a greater rate than the low curvature;

displaying, on a display device, the CBFV waveform comprising the morphology attributes; and highlighting the morphology attributes by displaying each of the two or more morphology indicators on or adjacent to corresponding one of the morphology attributes of the CBFV waveform, wherein the display device is configured to display the CBFV waveform and the two or more morphology indicators as the ultrasound data is being collected, wherein the two or more morphology indicators comprise the first morphology indicator highlighting high curvature at a first position of the CBFV waveform and the second morphology indicator highlighting low curvature at a second position of the CBFV waveform, and wherein the first morphology indicator and the second morphology indicator are graphically distinct, and determining that a patient is experiencing a medical condition based on the morphology indicators and configuring the display device to display a notification related to the medical condition.

18. The tool of claim 1, wherein each of the morphology indicators visually identifies an exact position of a corresponding one of the morphology attributes on the CBFV waveform.

* * * * *